(12) United States Patent
Pedersen et al.

(10) Patent No.: US 6,184,443 B1
(45) Date of Patent: Feb. 6, 2001

(54) COLD-INDUCIBLE AND TUBER-SPECIFIC PROMOTER SEQUENCE FROM POTATO α-AMYLASE GENE

(75) Inventors: Helle Frost Pedersen, deceased, late of Store Vorde Mou, by Rolf Frost Pedersen, legal representative; Marianne Lund, Galten; Finn Thuge Okkels; Jette Dina Kreiberg, both of Roskilde, all of (DK)

(73) Assignee: Danisco A/S, Copenhagen K (DK)

( * ) Notice: Under 35 U.S.C. 154(b), the term of this patent shall be extended for 0 days.

(21) Appl. No.: 08/817,913

(22) PCT Filed: Jun. 6, 1995

(86) PCT No.: PCT/EP95/02196

§ 371 Date: Sep. 15, 1997

§ 102(e) Date: Sep. 15, 1997

(87) PCT Pub. No.: WO96/12814

PCT Pub. Date: May 2, 1996

(30) Foreign Application Priority Data

Oct. 21, 1994 (GB) ................................................ 9421286

(51) Int. Cl.$^7$ ............................ A01H 5/00; C07H 21/04; C12N 5/14; C12N 15/82
(52) U.S. Cl. ................................... 800/317.2; 435/320.1; 435/419; 435/468; 536/24.1; 800/287; 800/298
(58) Field of Search .................... 435/69.1, 320.1, 435/419, 252.3, 468, 254.11; 536/24.1; 800/286, 287, 298, 317.2, 296, 295, 297

(56) References Cited

U.S. PATENT DOCUMENTS

| | | | |
|---|---|---|---|
| 5,436,393 | * | 7/1995 | Rocha-Sosa et al. ................. 800/205 |
| 5,705,375 | * | 1/1998 | Van Ooyen et al. ............. 435/172.3 |

FOREIGN PATENT DOCUMENTS

| | | |
|---|---|---|
| 2006454 | 12/1989 | (CA) . |
| 120 516 A2 | 2/1984 | (EP) . |
| 470 145 B1 | 4/1990 | (EP) . |
| 455 316 A2 | 4/1991 | (EP) . |
| WO 90/12876 | 11/1990 | (WO) . |
| WO 92/05259 | * 4/1992 | (WO) . |

OTHER PUBLICATIONS

Yamaguchi–Shinozaki K, et al. "A novel cis–acting element in an Arabidopsis gene is involved in responsiveness to drought, low–temperature, or high–salt stress." Plant Cell 6: 251–264, Feb. 1994.*
Baker SS, et al. "The 5'region of *Arabidopsis thaliana* cor15a has cis–acting elements that confer cold–, drought– and ABA–regulated gene expression." Plant Mol. Biol. 24: 701–713, Mar. 1994.*
Dolferus R, et al. "Regulation of the Arabidopsis Adh gene by anaerobic and other environmental stresses." Ann. Bot. 74: 301–308, Sep. 1994.*
Benfey PN, et al. "The cauliflower mosaic virus 35S promoter: Combinatorial regulation of transcription in plants." Science 250: 959–966, Nov. 1990.*
Kim Y, et al. "A 20 nucleotide upstream element is essential for the nopaline synthase (nos) promoter activity." Plant Mol. Biol. 24: 105–117, 1994.*
Fraley, Robert T.,et al.; CRC Critical Reviews in Plant Sciences; vol. 4, Issue 1; pp. 1–46; Genetic Transformation in Higher Plants 1986.
Gynheung, An, et al.; Plant Physiol. (1986) 81, pp. 301–305; Short Communication; Transformation of Tobacco, Tomato, Potato, and *Arabidopsis thaliana* Using a Binary Ti Vector System.
Matton, Daniel P., et al.; Plant Molecular Biology; 22: 279–291, 1993; Identification of cis–acting elements involved in the regulation of the pathogenesis–related gene STH–2 in potato.
Day, Mandy J. Dowson, et al.; Plant Molecular Biology 23: 97–109, 1993; Plant viral leaders influence expression of a reporter gene in tobacco.
Odell, Joan T., et al.; Letter to Nature, vol. 313, Feb. 28, 1985; pp. 810–813; Identification of DNA sequences required for activity of the cauliflower mosaic virus 35S promoter.
Murray, Noreen M., et al.; MGG, 150, 53–61 (1977); Lambdoid Phages that Simplify the Recovery of in vitro Recombinants.
Ueda, Takashi, et al.; The Plant Cell, vol. 1, 217–227; Feb. 1989, American Society of Plant Physiologists; Level of Expression of the Tomato rbcS–3A Gene is Modulated by a Far Upstream Promoter Element in a Developmentally Regulated Manner.
Borck, Kathleen, et al.; MGG, 146, 199–207 (1976); The Construction in vitro of Transducing Derivatives of Phage Lambda.
Fischer, Robert L., et al.; Cell, vol. 29, 651–660; Jun. 1982; Structure and Flanking Regions of Soybean Seed Protein Genes.
Yanisch–Perron, Celeste, et al.; Gene, 33 (1985) 103–119; Improved M13 phage cloning vectors and host strains: nucleotide sequences of the M13mp18 and pUC19 vectors.
Hoekema, A., et al.; Nature, vol. 303, May 12, 1983; A binary plant vector strategy based on separation of vir– and T–region of the *Agrobacterium tumefaciens* Ti–plasmid.
Linsmaier, Elfriede M., et al.; Physiologia Plantarum, vol. 18, 1965; Organic Growth Factor Requirements of Tobacco Tissue Cultures.
Murashige, Toshio, et al.; Physiologia Plantarum, vol. 15, 1962; A Revised Medium for Rapid Growth and Bio Assays with Tobacco Tissue Cultures.

(List continued on next page.)

Primary Examiner—Amy J. Nelson
(74) Attorney, Agent, or Firm—Knobbe, Martens, Olson & Bear, LLP

(57) ABSTRACT

A cold-inducible promoter region and a tuber-spec̈fic promoter region from an α-amylase gene from *Solanum tuberosum* are described. The promoter regions can be used to express a gene of interest in plants or plant cells.

19 Claims, 11 Drawing Sheets

OTHER PUBLICATIONS

Southern, E.M.; J. Mol. Biol. (1975) 98, 503–517; Detection of Specific Sequences Among DNA Fragments Separated by Gel Electrophoresis.

Bucher, Philipp, et al.; Nucleic Acids Research, vol. 14, No. 24, 1986; Compilation and analysis of eukaryotic POL II promoter sequences.

Butcher, D.N., et al.; Tissue Culture Methods for Plant Pathologists; pp. 203–208; 1980; The role of tissue culture in the study of crown–gall tumorigenesis.

Short, Jay M., et al.; Nucleic Acids Research; vol. 16, No. 15; 1988; ZAP: a bacteriophase expression vector with in vivo excision properties.

Potrykus, I.; Annu.Rev.Plant Physiol.Plant Mol.Biol. 1991; 42: 205–225; Gene Transfer to Plants: Assessment of Published Approaches and Results.

Bevan, Michael, et al.; Nucleic Acids Research; vol. 12, No. 22; 1984; Binary Agrobacterium vectors for plant transformation.

Chang, Hsin–Hsiung, et al.; Bot.Bull.Academia Sinica (1991) 32: 63–70; Improvement of potato (*Solanum tuberosum* L.) transformation efficiency by Agrobacterium in the presence of silver thiosulfate.

Holsters, M., et al.; Molec.Gen. Genet, 163, 181–187 (1978); Transfection and Transformation of *Agrobacterium tumefaciens*.

Jefferson, Richard A.; Plant Molecular Biology Reporter; vol. 5, No. 4; 1987; pp. 387–405; Assaying Chimeric Genes in Plants: The GUS Gene Fusion System.

Soberon, X., et al.; Gene, 9, (1980) 287–305; Construction and Characterization of New Cloning Vehicles.

Frischauf, Anna–Maria, et al.; J. Mol. Biol. (1983) 170, 827–842; Lambda Replacement Vectors Carrying Polylinker Sequences.

An, Grynheung, et al.; Plant Molecular Biology Manual A3: 1–19 (1988); Binary vectors.

Borton, K.A., et al.; Australia to Host 1994 International Dairy Congress; Agro–Food–Industry Hi–Tech; Mar./Apr. 1994; pp. 16–27.

Ohta, Shozo, et al.; MGG (1991) 225: 369–378; High–level expression of a sweet potato sporamin gene promoter: B–glucuroidase (GUS) fusion gene in the stems of transgenic tobacco plants is conferred by multiple cell type-specific regulatory elements.

Yamaguchi–Shinozaki, Kazuko, et al.; MGG (1993) 236: 331–340; Characterization of the expression of a desiccation–responsive rd29 gene of *ARabidopsis thaliana* and analysis of its promoter in transgenic plants.

Sleat, David E., et al.; Gene. 217 (1987) 217–225; Characterisation of the 5' –leader sequence of tobacco mosaic virus RNA as a general enhancer of translation in vitro.

Stougaard, Jens, et al.; Mol.Gen.Genet. (1990) 220: 353–360; Interdependence and nodule specificity of cis–acting regulatory elements in the soybean leghemoglobin lbc3 and N23 gene promoters.

Jefferson, Richard A., et al.; The EMBO Journal, vol. 6, No. 13. pp. 3901–3907; 1987; GUS fusions:B–glucuronidase as a sensitive and versatile gene fusion marker in higher plants.

Bevan, M.W., et al.; The EMBO Journal, vol. 4, No. 8, pp. 1921–1926; 1985; Expression of tobacco mosaic virus coat protein by a cauliflower mosaic virus promoter in plants transformed by Agrobacterium.

An, G., et al.; The EMBO Journal, vol. 4, No. 2, pp. 277–284; 1985; New cloning vehicles for transformation of higher plants.

Stougaard, Jens et al.; The EMBO Journal; vol. 6, No. 12, pp. 3565–3569; 1987; 5' Analysis of the soybean leghaemoglobin lbc3 gene: regulatory elements required for promoter activity and organ specificity.

Burow, Mark D., et al.; The Plant Journal (1992) 2(4), 537–548; Developmental control of the B–phaseolin gene requires positive, negative, and temporal seed–specific transcriptional regulatory elements and a negative element for stem and root expression.

Lorberth, Ruth, et al.; The Plant Journal, 1992; 2(4), 477–486; Promoter elements involved in environmental and developmental control of potato proteinase inhibitor II expression.

van der Steege, Gerrit, et al.; Plant Molecular Biology 20: 19–30, 1992; Potato granule–bound starch synthase promoter–controlled GUS expression: regulation of expression after transient and stable transformation.

Shah, Dilip M., et al.; Science, vol. 233,Jul. 25, 1986; 478–481; Engineering Herbicide Tolerance in Transgenic Plants.

Abel, Patricia Powell, et al.; Research Articles; Science, vol. 232: May 9, 1986; pp. 738–743; Delay of Disease Development in Transgenic Plants that Express the Tobacco Mosaic Virus Coat Protein Gene.

Cohen, S.N., et al.; Science, vol. 196, Apr. 8, 1977; pp. 180–183; Screening Agt Recombinant Clones by Hybridization to Single Placques in situ.

Tanida et al., "Functional Dissection of a Rice High–pI α–Amylase Gene Promoter," *Mol. Gen. Genet.,* 244:127–134 (1994).

* cited by examiner

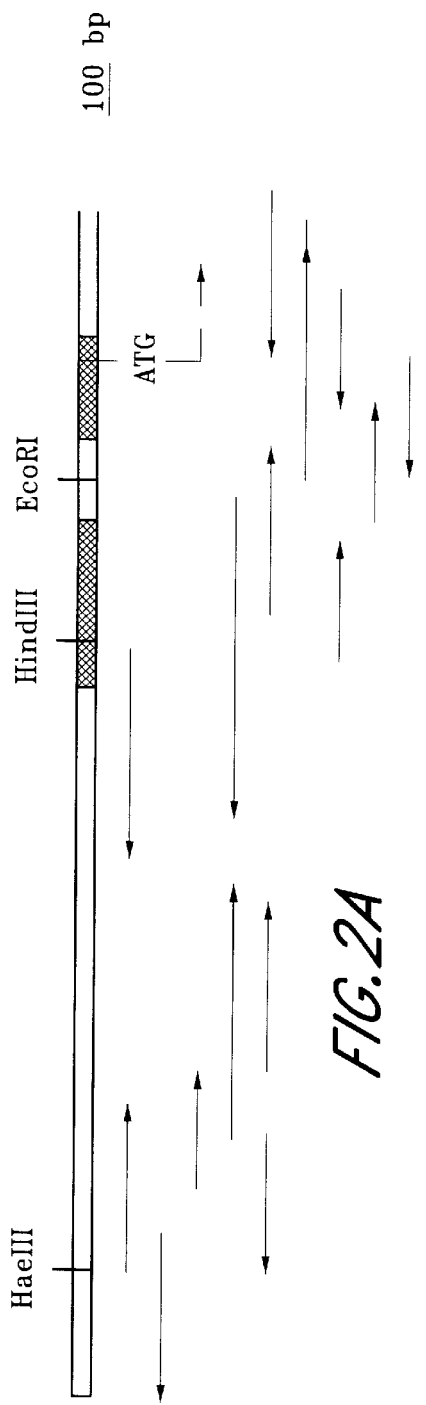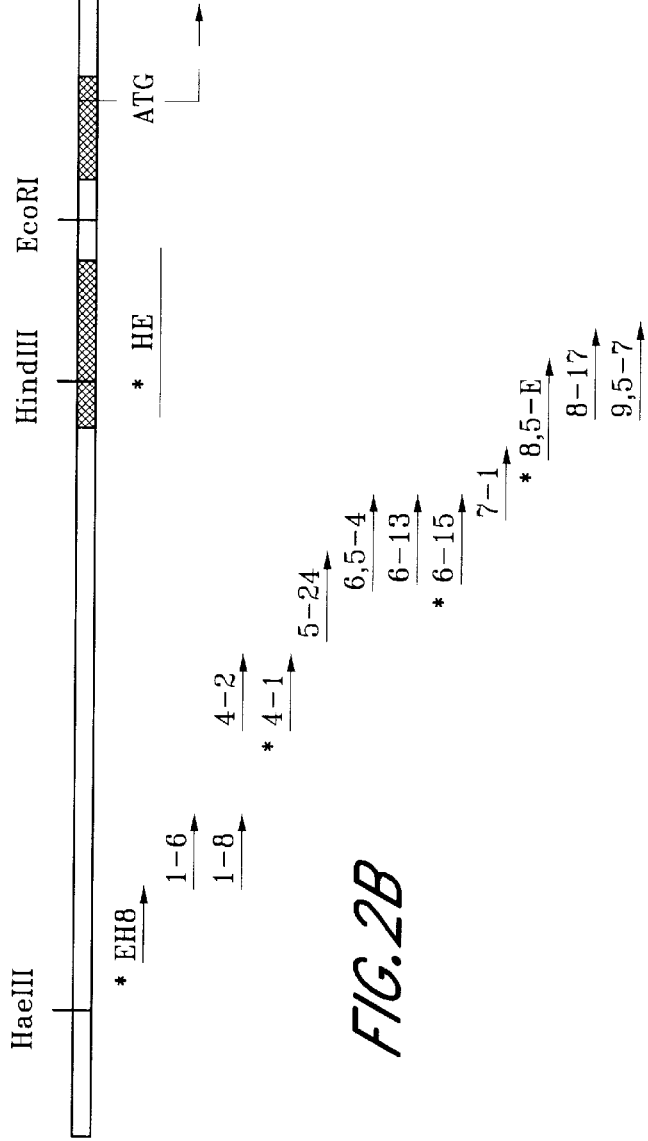
FIG.2A
FIG.2B

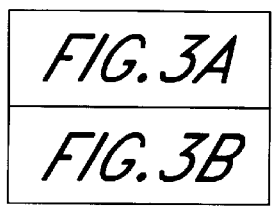

The α-Amy 3 promoter sequence.

```
- 1734   TCTTTAAGTTGTTTGCTTGATTTTTCTTCTTCAATCTTCTATATTTAATT
- 1684   CGTTTTAGCTTCAAACTTCTTCAATTTTATTTCAATTTAATTCTACAAAA
- 1634   AAAATCTCTATTTAGCACCATTCATAAAATTCATGCTCAAAATGGGCAAA
- 1584   CATAAATAATAAATGTGAAGTAAATAATGGATTAAAATATATATTTTTGG    Hae III
- 1534   GCCTCACATCAACCTTCATAATTCTTGAATGAATGAATGATAGACTTCAT
- 1484   AATTTTTAACCTATACATATAAGAAAATTGAGAGTAACTCAAATAACAA
- 1434   GTTGTAGTATCACATCTTTACTATTTGATAACATTATGAAGGTGATTATA
- 1384   CATTACGTAACATTTCTTTTAAAAATATGTAAGCAAATTTACTTTTTAAC
- 1334   TTATCATTGATCTTCATGGTTTTGTCATAAATCTCAAAGTTATCATATTT
- 1284   TATATAGCTATTTGAAAGTAATTTTATTTTTACTCATCATTGAGTGATGC
- 1234   TTTTATTATAATACTAGTAAGTTTTATTTATTATTTTCTTTTAGGGGTGA
- 1184   ATTGTATAATATAATAAAAATATATTTTTAGAAATAATGATTCTTTTAT
- 1134   TATTAAAAGTTAAGATATTAGATTATTTATGCTTGTATAATAATGAACG
- 1084   AAGTTTTATTTTCTATGAGTTTCATTAATCATGTTTGTAATTATTTCAAA
- 1034   TTTTGATGTATTTTTATAATTTTGTATTATTATATTATTATACTATATTT
-  984   AAAAATTTAAAGATCCATAGGGCTTACGCCCCACGTCAAGAGGCTTGGGG
-  934   CTTTCCCTAAATTAAGTAAAACTCTTCGCCTCATGCCTTACGCCTCCGCC
-  884   TTTTAAAACACTGATTCCTTTCCTCATATAGCTTGAGGCGAAAATATTTA
-  834   ATAAAAACACTTCTTAATTTGTTTATATGTTCAATTGAACATGTCCGTGA
-  784   TTAGAAAATTAAATTAAATTCAATGACAAATTTAATAATTTGACACAAAA
-  734   TTTATGAAAAAAATATCAAAATATAAGAAATATTTTTTTTGAAATGGAT
-  684   TAAAAGAAAAAAAAAACAAATAAATTGAACCGGGATAAGTTGGTTGTTT
-  634   AATTGATTATTGATTATGATCTCAATTTGACATTTTGCGCGATCTTTCGA
-  584   CCTCAATTCGTATGAACTGACACTACGCCAATGGACAGTCGCCGTCGTCA
-  534   CCGCCACCGCACTATTCTCGACGCGTCGTCTATCTCCTCCACCCCACAGC
```

```
              Hind III
- 484    CGTCAATTCCAAGCTTCCAATGAACCGTTGCCATGTGTCACTGCCTATTC
- 434    ACCGCGAAAC ATGAATATCACTGACGAACGATTTCGGAGCGGAACGAATC
                                                    CAP site
- 384    CAGAAAATGGATTACTTTCTATAAATTCCTCGAATCTCAACTCCATTTCG   U
                                                              N
                                                              T
- 334    TAAAAATAAAATTAAAAATATTGTTTCTTTTTGTATTTCTTTTTGTATTT   R
                                                              A
- 284    CTGGTTTATGTGGTGATCGAATTTTCAATTTTTTACTGGTAGTGATTCC   N
                                                       Eco RI S   L
- 234    CTGGTTTATGTGGTGATCGAATTTTCAATTTTTTACTGGTAGTGATTCC   L   E
                                                              A   A
- 184    CATGATTCCTTATCAGAGGAATCGATCCGATTTGACTAATTTCACTTTTC   T   D
                                                              E   E
- 134    AGCAAGGGACGTATAATCTCAACTACAATCCATT                   D   R
         +1                                       -1
+   1    ATGGCGCTTGATGAAAGTCAGCAGTCTGATCCATGTAAGGTTCTCTTTTC
+  51    CTTTATATATGCTTCATAATTGAGAAGGAAGACGGAGATTTGAACTTAAT
+ 101    AAAGGCGAAGATTTGAACAAAATATTTTGGTATTTCATTTAAAACTTTAC
+ 151    CAGTTCTAAGAGTAAATGATTGGGATGTGCATGTCC.......
```

Restriction sites are bold faced. TATA, CCAAT, and ATG are underlined
The position of the proposed CAP site and the untranslated leader
sequence are indicated.

Select deletions of the α-Amy 3 promoter for functional analysis.

Primer sequences

| Name | 5' – Sequence – 3' |
|------|---------------------|
| P1 | GATAACATTATGAAGGTGAT |
| P2 | GACGGCTGTGGGGTGGAGGAG |
| P3 | CTTGTTATTTGAGTTACTCTC |
| P7A | CATAAATTTGTGTCAAATTATTAAAT |
| P8 | AGGGGTGAATTGTATAATATAAT |
| P10 | GAAATATTTTTTTGAAATGGAT |
| P11 | ATTATATTATACAATTCACCCCT |

Uni = T7 primer

Rev = T3 primer

| #589 | CGCTTTCCCACCAACGCTGAT |

FIG. 6

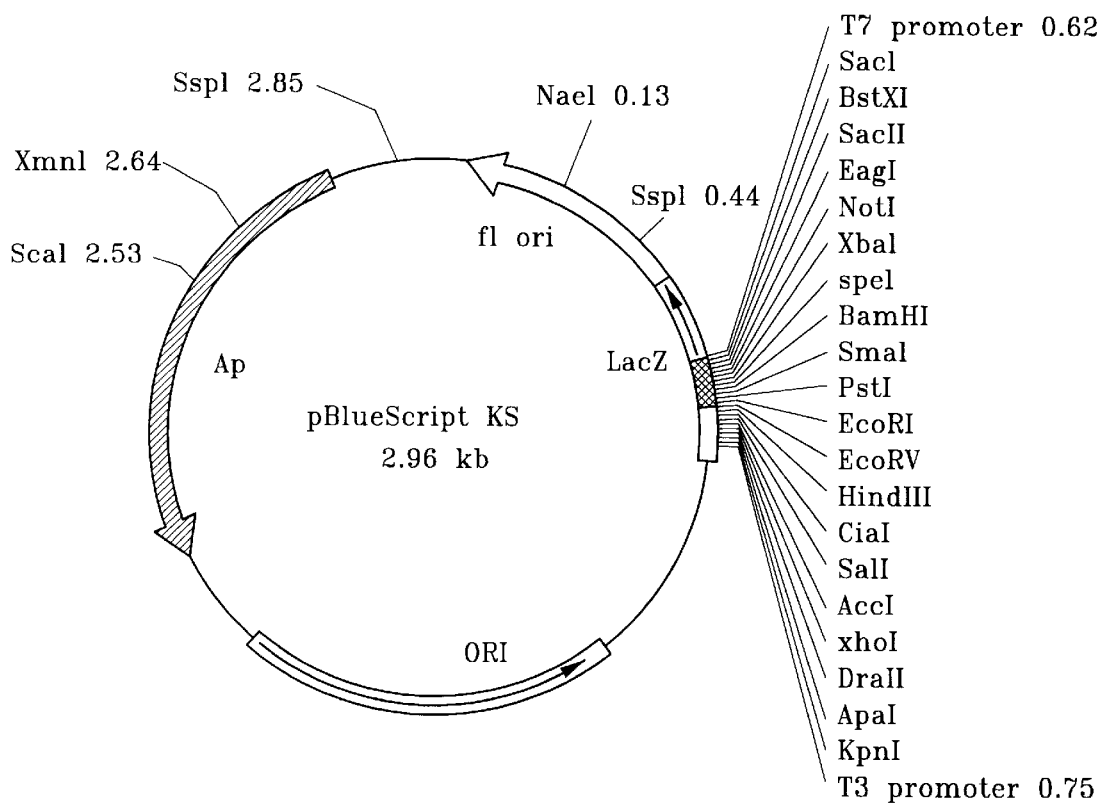
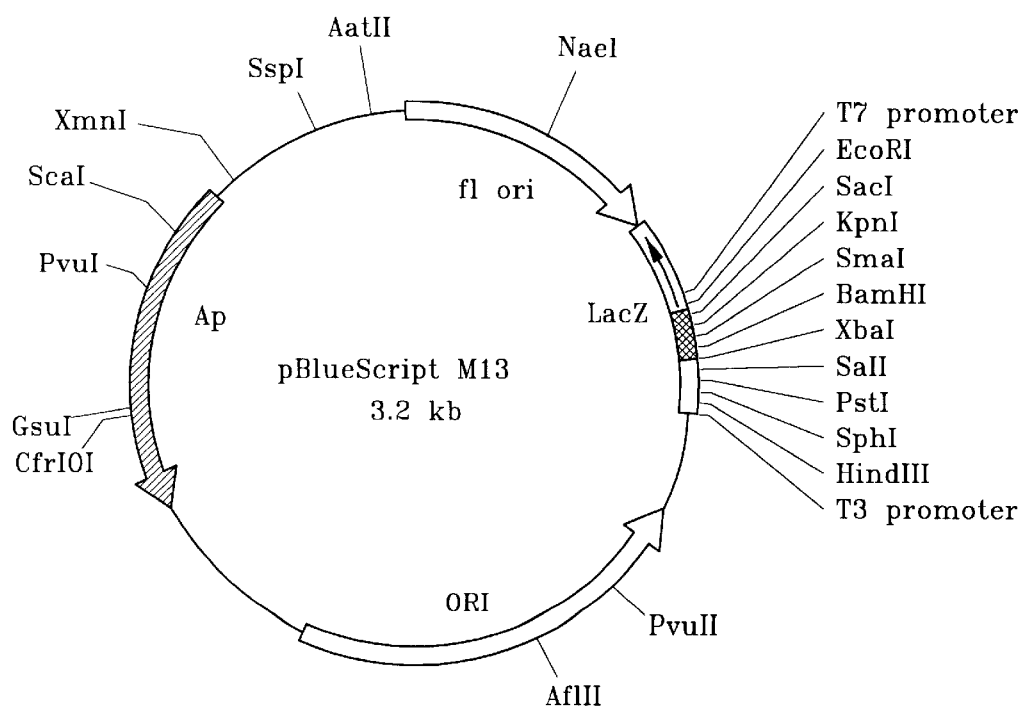
FIG. 7

COLD-INDUCIBLE AND TUBER-SPECIFIC PROMOTER SEQUENCE FROM POTATO α-AMYLASE GENE

This is the U.S. national phase under 35 U.S.C. § 371 of International Application PCT/EP95/02196, filed Jun. 6, 1995.

FIELD OF THE INVENTION

The present invention relates to a promoter, including a construct and an expression vector comprising the same and a transformed cell comprising the same. In addition the present invention relates to a plant comprising the same.

BACKGROUND OF THE INVENTION

It is known that it is desirable to direct expression of a gene of interest ("GOI") in certain tissues of an organism—such as a plant. For example, it may be desirable to produce crop protein products with an optimised amino acid composition and so increase the nutritive value of the crop. It may even be desirable to use the crop to express non-plant genes such as genes for mammalian products. Examples of the latter products include interferons, insulin, blood factors and plasminogen activators.

However, whilst it may be desirable to achieve expression of a GOI in certain tissues it is sometimes important (if not necessary) to ensure that the GOI is not expressed in other tissues in such a manner that detrimental effects may occur. Moreover, it is important not to upset the normal metabolism of the organism to such an extent that detrimental effects occur. For example, a disturbance in the normal metabolism in a plant's leaf or root tip could lead to stunted growth of the plant.

CA-A-2006454 describes a DNA sequence of an expression cassette in which the potato tuber specific regulatory regions are localised. The expression cassette contains a patatin-gene with a patatin-gene promoter. The DNA sequence is transferred into a plant genome using agrobacteria. According to CA-A-2006454, the DNA sequence enables heterologous products to be prepared in crops.

One of the key plant enzymes is α-amylase. α-amylase participates in the pathway responsible for the breakdown of starch to reducing sugars in potato tubers. Genes coding for α-amylase in potato plants have been isolated and characterised. For example, see the teachings in EP-B-0470145.

In brief, α-amylase is encoded by a gene family consisting of at least 5 individual genes. Based on their homology the genes can be divided into two subfamilies—one of which is the type 3 amylase(s), the other of which is the type 1 amylase(s). The two groups of α-amylases are expressed differently, not only on the molecular level but also in different tissues of the potato plant.

In this regard, type 3 α-amylases are expressed in root, in tubers, in sprouts and in stem tissue; whereas type 1 α-amylases are expressed in sprout and stem tissues, but not in tubers.

SUMMARY OF THE INVENTION

The present invention seeks to provide a plant promoter that is capable of directing the expression of a gene of interest in specific tissues, or in just a specific tissue, of an organism, typically a plant.

According to a first aspect of the present invention there is provided a promoter comprising a nucleotide sequence corresponding to the 5.5 Kb EcoR1 fragment isolated from *Solanum tuberosum*, or a variant, homologue or fragment thereof.

A restriction map of the 5.5 Kb EcoR1 fragment isolated from *Solanum tuberosum* is shown in FIGS. 1, 2 and 8—which are discussed later.

According to a second aspect of the present invention there is provided a promoter comprising a nucleotide sequence corresponding to the 5.5 Kb EcoR1 fragment isolated from *Solanum tuberosum*, or a variant, homologue or fragment thereof but wherein at least a part of the promoter is inactivated.

According to a third aspect of the present invention there is provided a promoter comprising at least the nucleotide sequence shown as SEQ ID NO:1 or a variant, homologue or fragment thereof.

According to a fourth aspect of the present invention there is provided a promoter comprising the nucleotide sequence of any of one of the sequences shown as Seq.I.D.No.s 4–17, preferably any of one of the sequences shown as Seq.I.D.No.s 4–16, or a variant, homologue or fragment thereof.

According to a fifth aspect of the present invention there is provided a promoter comprising a nucleotide sequence corresponding to the 5.5. Kb EcoR1 fragment isolated from *Solanum tuberosum*, or a variant, homologue or fragment thereof, but wherein at least the nucleotide sequence shown as SEQ ID NO:1 is inactivated.

According to a sixth aspect of the present invention there is provided a promoter comprising a nucleotide sequence corresponding to the 5.5. Kb EcoR1 fragment isolated from *Solanum tuberosum*, or a variant, homologue or fragment thereof, but wherein at least any of one of the sequences shown as SEQ ID NOS:2–16 is inactivated.

According to a seventh aspect of the present invention there is provided a construct comprising the promoter according to the present invention fused to a GOI.

According to an eighth aspect of the present invention there is provided an expression vector comprising the promoter according to the present invention.

According to a ninth aspect of the present invention there is provided a transformation vector comprising the promoter according to the present invention.

According to a tenth aspect of the present invention there is provided a transformed cell comprising the promoter according to the present invention.

According to an eleventh aspect of the present invention there is provided a transgenic organism comprising the promoter according to the present invention.

According to a twelfth aspect of the present invention there is provided the use of the promoter according to the present invention as a cold inducible promoter.

According to a thirteenth aspect of the present invention there is provided a construct comprising the promoter of the present invention and a nucleotide sequence coding for anti-sense alpha-amylase.

According to a fourteenth aspect of the present invention there is provided the use of a promoter according to the present invention for expressing a GOI in tuber and/or sprout and/or root and/or stem of a plant, preferably in just or at least tuber of a plant.

Other aspects of the present invention include methods of expressing or transforming any one of the expression vector, the transformation vector, the transformed cell, including in situ expression within the transgenic organism, as well as the products thereof. Additional aspects of the present invention include uses of the promoters for expressing GOIs in vitro (e.g. in culture media such as a broth) and in vivo (e.g. in a transgenic organism).

Preferably, in any one of the expression vector, the transformation vector, the transformed cell or the transgenic organism the promoter is present in combination with at least one GOI.

Preferably the transformation vector is derived from agrobacterium.

Preferably the promoter is stably incorporated within the transgenic organism's genome.

Preferably the transgenic organism is a plant. Preferably the plant is a dicot plant.

More preferably, the plant is a potato plant.

BRIEF DESCRIPTION OF THE FIGURES

FIG. 2 shows a restriction enzyme map;

FIG. 3 shows a nucleotide sequence of a promoter according to the present invention;

FIG. 6 shows a series of primer sequences;

FIG. 7 shows a map of pBlueScript KS (2.96 kb) and a map of pBlueScript M13 (3.2 kb).

DETAILED DESCRIPTION OF THE INVENTION

Figure 1:
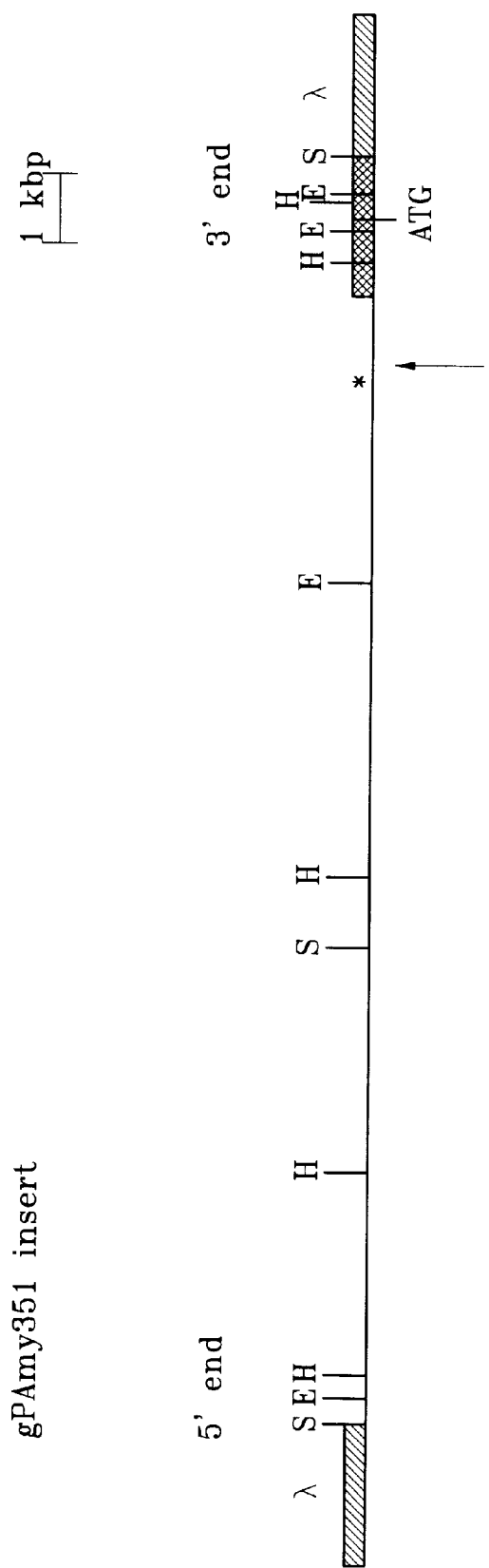
FIG. 1 shows a restriction enzyme map.

An advantage of the present invention is that a promoter corresponding to the 5.5. Kb EcoR1 fragment isolated from *Solanum tuberosum* is able to direct expression of a GOI in any one of root, tuber, sprout and stem tissue of a dicot, for example, a potato. The same is true for the variant, homologue or fragment thereof.

Further surprising however is the fact that at least a part of the promoter sequence can be inactivated (e.g. truncated) and it can still express a GOI.

More surprising is the fact that the partially inactivated (e.g. truncated) promoter sequences can direct expression of a GOI in one or more specific tissues, such as just tuber tissue, rather than in combination of root, tuber, sprout and stem tissues.

In this regard, it was found that modified promoters corresponding to the 5.5 Kb EcoR1 fragment isolated from *Solanum tuberosum* containing inactivated nucleotide sequences upstream (i.e. towards the 5' end) of position −691 with reference to FIG. 3 do not yield expression in any one of root, tuber, sprout or stem tissue. Examples of such modified promoters include modified promoters containing only nucleotide sequences downstream of position −692, such as the promoter sequences SEQ ID NOS:2–3.

However, it was found that promoters corresponding to the 5.5 Kb EcoR1 fragment isolated from *Solanum tuberosum* containing inactivated nucleotide sequences upstream of position −1535 (with reference to FIG. 3) yield expression only in tuber tissue. Examples of these types of promoters include those that contain only nucleotide sequences downstream of position −1535 but wherein they contain at least nucleotide sequences upstream of −691 (with reference to FIG. 3), such as the promoter sequences SEQ ID NOS:4–17, in particular SEQ ID NOS:6–17, more in particular SEQ ID NOS:6–16.

Moreover, it was found with the last type of promoters that if those promoters contained at least SEQ ID NO:1 high expression yields were observed in tuber tissue.

Thus preferred examples of promoter sequences for tuber specific expression of a GOI containing at least the sequence shown as SEQ ID NO:1 include those sequences shown as Seq. I.D. No.s 4–17, more preferably those sequences shown as SEQ ID NOS:6–17, even more preferably those sequences shown as SEQ ID NOS:6–16.

Furthermore, it was found that promoters corresponding to the 5.5 Kb EcoR1 fragment isolated from *Solanum tuberosum* containing inactivated nucleotide sequences downstream of position −1535 (with reference to FIG. 3) yield expression in root and/or sprout and/or stem tissue. Examples of these types of promoters include those that contain only nucleotide sequences upstream of position −1535 (with reference to FIG. 3).

Moreover, it was found that promoters corresponding to the 5.5 Kb EcoR1 fragment isolated from *Solanum tuberosum* containing an inactive SEQ ID NO:1 yield expression only in root and/or sprout and/or stem tissue. Examples of these types of promoters include those that do not contain Seq. I.D. No. 1.

Particularly preferred sequences are SEQ ID NOS:4–16.

Tissue specific expression, such as tuber specific expression, is particularly advantageous for a number of reasons.

First, a GOI (as defined below) can be expressed in a specific tissue type. This is particularly advantageous if the GOI is an anti-sense endogenous for the organism in question because expression of the anti-sense sequence in other tissues can be detrimental.

Second, it is possible to express a GOI coding for an agent giving the organism resistance against a disease associated with specific tissue(s). For example, the GOI may be a toxin against common scab—which normally affects tuber tissue.

Third, large quantities of the product of expression of a GOI where the GOI is, for example, a desired compound of benefit to humans or animals (e.g. a desirable foodstuff or an enzyme having a beneficial pharmaceutical effect) can be achieved. Furthermore, that product is easily retrievable.

Fourth, use of the promoter according to the present invention enables one to express a suitable nucleotide in order to change the organism's metabolism at a specific site—such as increasing starch levels in tuber or even producing modified starch therein.

A further surprising advantage is that the promoter of the present invention, in particular the promoter of the first aspect of the present invention, is cold-inducible—i.e. leads to expression in conditions of about from 0° C. to 12° C., to about 4° C. Thus this promoter is very useful for expressing GOI's in conditions that would be of some benefit in cold conditions—in particular such as expression of the alpha—amylase gene (or active fragment thereof) of EP-B-0470145 (shown as SEQ ID NO:18). More preferably the GOI is a nucleotide sequence that is anti-sense to that alpha-amylase gene (or active fragment thereof), such as that shown as SEQ ID NO:19.

Highly preferred embodiments of each of the aspects of the present invention do not include the native promoter in its natural environment.

The term "promoter" is used in the normal sense of the art, e.g. an RNA polymerase binding site in the Jacob-Monod theory of gene expression. The promoters of the present invention are capable of expressing a GOI. In addition to the nucleotide sequences described above, the promoters of the present invention could additionally include conserved regions such as a Pribnow Box or a TATA box. The promoters may even contain other sequences to affect (such as to maintain, enhance, decrease) the levels of expression of the GOI. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' leader sequence (see Sleat Gene 217 [1987] 217–225; and Dawson Plant Mol. Biol. 23 [1993] 97). The promoter of the present invention may also be called Amy 3 promoter or Amy 351 promoter or alpha-Amy 351 promoter or alpha-Amy 3 promoter.

In addition the present invention also encompasses combinations of promoters or elements.

For example, a promoter of the present invention, such as a tuber specific promoter (see above), may be used in combination with a stem specific promoter (see above). Other combinations are possible. For example, the promoter of the present invention, such as a stem or tuber specific promoter, may be used in combination with a root promoter and/or a leaf promoter.

The term "corresponding" in relation to the present invention means that the promoter sequence need not necessarily be derived from *Solanum tuberosum*. For example, the promoter could be prepared synthetically. It may even be derived from another source.

The terms "variant", "homologue" or "fragment" include any substitution of, variation of, modification of, replacement of, deletion of or addition of one (or more) nucleic acid from or to the sequence providing the resultant nucleotide sequence has the ability to act as a promoter in an expression system—such as the transformed cell or transgenic organism according to the present invention. In particular, the term "homologue" covers homology with respect to structure and/or function providing the resultant nucleotide sequence has the ability to act as a promoter. With respect to sequence homology, preferably there is at least 75%, more preferably at least 85%, more preferably at least 90% homology, more preferably at least 95%, more preferably at least 98% homology.

Figure 8:
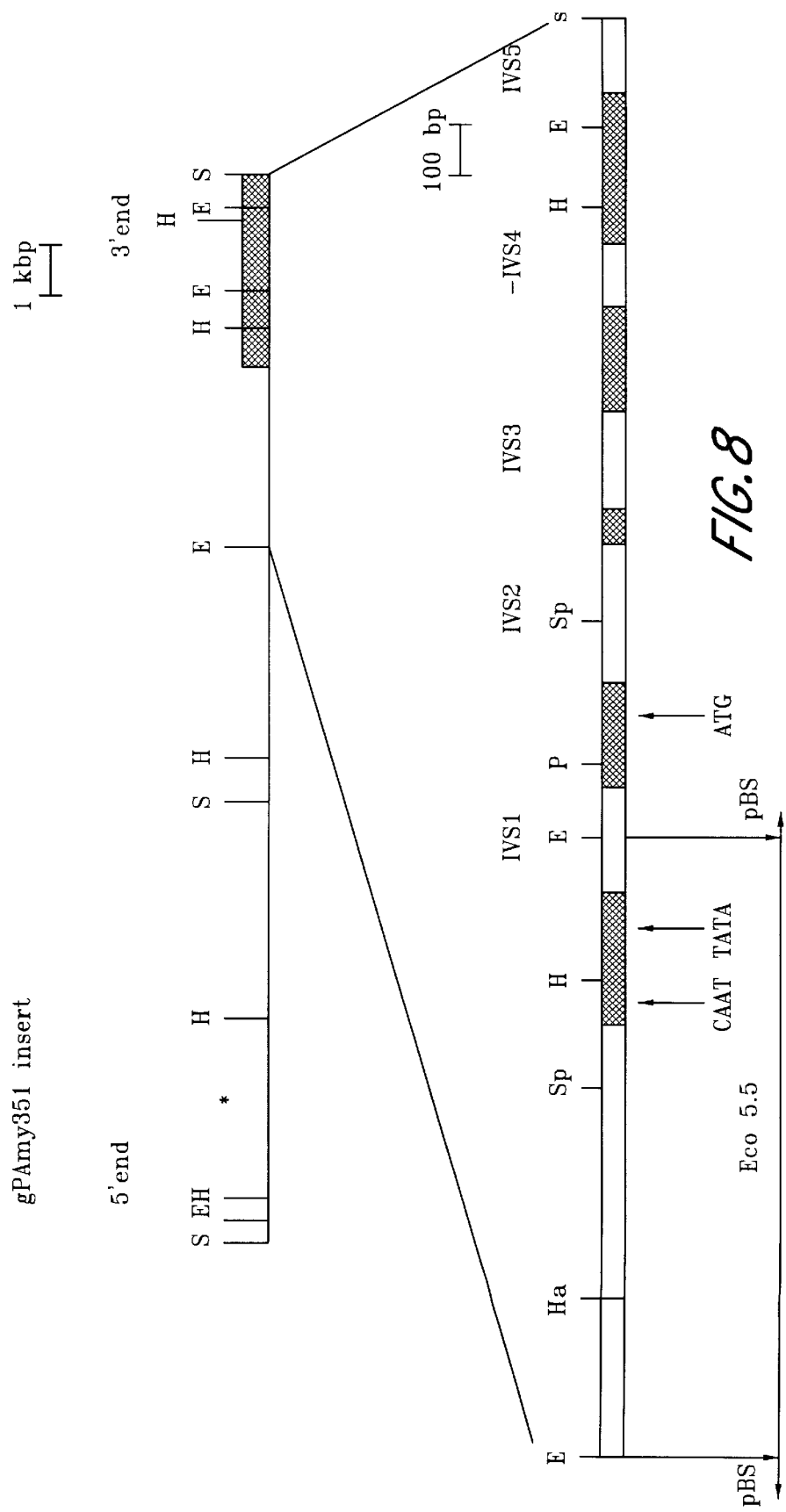
FIG. 8 is a restriction enzyme map.

The term "inactivated" means partial inactivation in the sense that the expression pattern of the complete promoter of FIG. 8 is modified but wherein the partially inactivated promoter still functions as a promoter. However, as mentioned above, the modified promoter is capable of expressing a GOI in at least one (but not all) specific tissue of the complete promoter of FIG. 8. Therefore with this particular aspect of the invention, the promoter having an inactivated portion can still function as a promoter (hence it is still called a promoter) but wherein the promoter is capable of expressing a GOI in one or more, but not all, of the tissues where a GOI is expressed by the complete promoter shown in FIG. 8.

Examples of partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part.

Accordingly, for a preferred embodiment of the present invention there is provided a promoter comprising a nucleotide sequence corresponding to the 5.5 Kb EcoR1 fragment isolated from *Solanum tuberosum*, or a variant, homologue or fragment thereof but wherein the promoter is truncated. The term "truncated" includes shortened versions of the promoter shown in FIG. 8.

Accordingly, for a preferred embodiment of the present invention there is also provided a promoter comprising a nucleotide sequence corresponding to the 5.5. Kb EcoR1 fragment isolated from *Solanum tuberosum*, or a variant, homologue or fragment thereof, but wherein the promoter does not contain at least the nucleotide sequence of any of one the sequences shown as SEQ ID NOS:4–16.

Furthermore, for a preferred embodiment of the present invention there is also provided a promoter comprising a nucleotide sequence corresponding to the 5.5. Kb EcoR1 fragment isolated from *Solanum tuberosum*, or a variant, homologue or fragment thereof, but wherein the promoter does not contain at least the nucleotide sequence shown as SEQ ID NOS:1.

The term "construct"—which is synonymous with terms such as "conjugate", "cassette" and "hybrid"—includes a GOI directly or indirectly attached to the promoter. An example of an indirect attachment is the provision of a suitable spacer group such as an intron sequence, such as the Sh1-intron or the ADH intron, intermediate the promoter and the GOI. The same is true for the term "fused" in relation to the present invention which includes direct or indirect attachment. In each case, it is highly preferred that the terms do not cover the natural combination of the wild type alpha amylase gene ordinarily associated with the wild type gene promoter and the wild type promoter and when they are both in their natural environment.

The construct may even contain or express a marker which allows for the selection of the genetic construct in, for example, a plant cell into which it has been transferred. Various markers exist which may be used in, for example, plants—such as mannose. Other examples of markers include those that provide for antibiotic resistance—such as resistance to G418, hygromycin, bleomycin, kanamycin and gentamycin.

The term "GOI" with reference to the present invention means any gene of interest. A GOI can be any nucleotide that is either foreign or natural to the organism (e.g. plant) in question.

Typical examples of a GOI include genes encoding for proteins and enzymes that modify metabolic and catabolic processes. For example, the GOI may be a protein giving added nutritional value to the plant as a food or crop. Typical examples include plant proteins that can inhibit the formation of anti-nutritive factors and plant proteins that have a more desirable amino acid composition (e.g. a higher lysine content than the non-transgenic plant).

The GOI may even code for an enzyme that can be used in food processing such as chymosin, thaumatin and alpha-galactosidase. The GOI may even code for an agent for introducing or increasing pathogen resistance. The GOI may even be an antisense construct for modifying the expression of natural transcripts present in the relevant tissues.

The GOI may even code for a non-natural plant compound that is of benefit to animals or humans. For example, the GOI could code for a pharmaceutically active protein or enzyme such as any one of the therapeutic compounds insulin, interferon, human serum albumin, human growth factor and blood clotting factors. In this regard, the transformed cell or organism could prepare acceptable quantities of the desired compound which would be easily retrievable from, for example, the tubers.

Preferably the GOI is a gene encoding for any one of a protein having a high nutritional value, a pest toxin, an antisense transcript such as that for patatin, ADP-glucose pyrophosphorylase (e.g. see EP-A-455316), alpha-amylase (e.g. see EP-B-0470145), a protease antisense or a glucanase. A preferred GOI is an anti-sense sequence to the alpha-amylase gene described in EP-B-0470145.

The term 'organism' in relation to the present invention includes any organism that can activate the promoter of the present invention, such as amylase (e.g. alpha-amylase) producing organisms including plants, algae, fungi and bacteria, as well as cell lines thereof. Preferably the term means a plant or cell thereof, preferably a dicot, more preferably a potato.

The term 'transgenic organism' in relation to the present invention means an organism comprising either an expressable construct according to the present invention or a product of such a construct. For example the transgenic organism can comprise an exogenous nucleotide sequence (e.g. GOI as herein described) under the control of a promoter according to the present invention; or a native nucleotide sequence under the control of a partially inactivated (e.g. truncated) promoter according to the present invention.

The terms "cell", "tissue" and "organ" include cell, tissue and organ per se and when within an organism. For one class/type of promoters according to the present invention the term means potato tuber cell, tissue or organ and/or potato root cell, tissue or organ and/or potato sprout cell, tissue or organ and/or potato stem cell, tissue or organ. Preferably, the term means means just or at least a potato tuber cell, tissue or organ.

Preferably the expressable construct is incorporated in the genome of the organism. The term incorporated preferably covers stable incorporation into the genome.

The term 'nucleotide' in relation to the GOI includes genomic DNA, cDNA, synthetic DNA, and RNA. Preferably it means DNA, more preferably cDNA.

The term "expression vector" means a construct capable of in vivo or in vitro expression.

The term "transformation vector" means a construct capable of being transferred from one species to another—such as from an *E. Coli* plasmid to a plant cell.

Even though the promoters of the present invention are not disclosed in EP-B-0470145 and CA-A-2006454, those two documents do provide some useful background commentary on the types of techniques that may be employed to put the present invention into practice.

Some of these background teachings are included in the following commentary.

The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

Thus, in one aspect, the present invention relates to a vector system which carries a promoter or construct according to the present invention and which is capable of introducing the promoter or construct into the genome of a plant such as a plant of the family Solanaceae, in particular of the genus Solanum, especially *Solanum tuberosum*.

The vector system may comprise one vector, but comprises preferably two vectors; in the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or construct is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists*, eds.: D. S. Ingrams and J. P. Helgeson, 203–208.

Several different Ti and Ri plasmids have been constructed which are suitable for the construction of the plant or plant cell constructs described above. A non-limiting example of such a Ti plasmid is pGV3850.

The promoter or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, the vector system of the present invention is preferably one which contains the sequences necessary to infect a plant (e.g. the vir region) and at least one border part of a T-DNA sequence, the border part being located on the same vector as the genetic construct. Furthermore, the vector system is preferably an *Agrobacterium tumefaciens* Ti-plasmid or an *Agrobacterium rhizogenes* Ri-plasmid or a derivative thereof, as these plasmids are well-known and widely employed in the construction of transgenic plants, many vector systems exist which are based on these plasmids or derivatives thereof.

In the construction of a transgenic plant the promoter or construct may be first constructed in a microorganism in which the vector can replicate and which is easy to manipulate before insertion into the plant. An example of a useful microorganism is *E. coli*, but other microorganisms having the above properties may be used. When a vector of a vector system as defined above has been constructed in *E. coli*, it is transferred, if necessary, into a suitable Agrobacterium strain, e.g. *Agrobacterium tumefaciens*.

The Ti-plasmid harbouring the promoter or construct of the invention is thus preferably transferred into a suitable Agrobacterium strain, e.g. *A. tumefaciens*, so as to obtain an Agrobacterium cell harbouring the promoter or construct of the invention, which DNA is subsequently transferred into the plant cell to be modified.

Direct infection of plant tissues by Agrobacterium is a simple technique which has been widely employed and which is described in Butcher D. N. et al. (1980), *Tissue Culture Methods for Plant Pathologists*, eds.: D. S. Ingrams and J. P. Helgeson, 203–208. See also Potrykus (Annu Rev Plant Physiol Plant Mol Biol [1991] 42:205–225) and Christou (Agro-Food-Industry Hi-Tech March/April 1994 17–27).

As reported in CA-A-2006454, a large amount of cloning vectors are available which contain a replication system in *E. coli* and a marker which allows a selection of the transformed cells. The vectors contain for example pBR 332, pUC series, M13 mp series, pACYC 184 etc. In such a way, the construct or promoter can be introduced into a suitable restriction position in the vector. The contained plasmid is used for the transformation in *E. coli*. The *E. coli* cells are cultivated in a suitable nutrient medium and then harvested and lysed. The plasmid is then recovered. As a method of analysis there is generally used a sequence analysis, a restriction analysis, electrophoresis and further biochemical-molecular biological methods. After each manipulation, the used DNA sequence can be restricted and connected with the next DNA sequence. Each sequence can be cloned in the same or different plasmid. After each introduction method of the desired promoter or construct in the plants further DNA sequences may be necessary. If for example for the transformation, the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells is being intensively studied and is well described in EP 120 516; Hoekema, in: The Binary Plant Vector System Offset-drukkerij Kanters B. B., Alblasserdam, 1985, Chapter V; Fraley, et al., Crit. Rev. Plant Sci., 4:1–46 and An et al., EMBO J. (1985) 4:277–284.

Direct infection of plant tissues by Agrobacterium is another simple technique which may be employed. Typically, a plant to be infected is wounded, e.g. by cutting the plant with a razor or puncturing the plant with a needle or rubbing the plant with an abrasive. The wound is then inoculated with the Agrobacterium, e.g. in a solution. Alternatively, the infection of a plant may be done on a certain part or tissue of the plant, i.e. on a part of a leaf, a root, a stem or another part of the plant. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

In summation therefore the present invention therefore relates to a promoter and, also to a construct comprising the same. In particular the present invention relates to the use of a promoter for the expression of a GOI in an cell/tissue/organism such as one or more specific tissues of a plant, in particular a dicot plant such as a potato.

More in particular, in a preferred embodiment, the present invention relates to a partially inactivated (such as truncated) type 3 α-amylase promoter.

The present invention also relates to the application of one class of partially inactivated gene promoters to express a GOI specifically in the tuber tissue of a dicot—especially a potato plant.

The following sample has been deposited in accordance with the Budapest Treaty at the recognised depositary The National Collections of Industrial and Marine Bacteria Limited (NCIMB) at 23 St Machar Drive, Aberdeen, Scotland, AB2 1RY, United Kingdom, on Aug. 26, 1994:

DH5alpha-gPAmy 351 (Deposit No. NCIMB 40682).

This sample is an *E. Coli* bacterial stock containing the plasmid pBluescript (see FIG. 7 for a general map thereof) containing an EcoR1 5.5 genomic DNA fragment isolated from potato (*Solanum tuberosum*). The EcoR1 5.5 fragment contains the promoter region and part of the 5' untranslated sequence of the structural gene of a potato alpha-amylase gene. The plasmid was formed by inserting the EcoR1 5.5 kb potato fragment into the polylinker of the vector pBS (Short et al [1988] Nuc. Acid. Res. 16:7583–7600). The promoter may be isolated from the plasmid by enzyme digestion with EcoR1 and then extracted by typical separation techniques (e.g. gels).

The following sample has been deposited in accordance with the Budapest Treaty at the recognised depositary The National Collections of Industrial and Marine Bacteria Limited (NCIMB) at 23 St Machar Drive, Aberdeen, Scotland, AB2 1RY, United Kingdom, on Oct. 20, 1994:

DH5alpha-pJK4 (Deposit No. NCIMB 40691).

This sample is an *E. Coli* bacterial (DH5alpha-) stock containing plasmid pJK4 (described later).

The present invention will now be described only by way of examples in which reference is made to the Figures.

In more detail, FIG. 1 is a restriction enzyme map of genomic clone gPAmy 351 isolated from the potato variety Saturna, in which the arrow indicates the position of the promoter, the closed bar indicates the position of coding sequences, H=HindIII, E=EcoRI, S=SalI, ATG=initiation codon of the alpha-amylase coding sequence and A star marks the position of the 5.5 kb EcoRI fragment.

FIG. 2 is a sequence map of the alpha-Amy 3 promoter in which the arrows show the extent of the sequence reactions, the position of the HE fragment is shown in B together with the 5' sequenced part of the promoter deletion series, the names of the individual fragments (see also FIG. 4) are given above the arrows, ATG=initiation codon of the alpha-amylase coding sequence, and the deletion fragments chosen for functional analysis are indicated by asterisks.

FIG. 3 is a nucleotide sequence of part of the alpha-Amy 3 promoter in which the restriction sites are bold faced, TATA, CCAAT and ATG sites are underlined, the position of the proposed CAP site and the untranslated leader sequence are indicated, and the 166 bp nucleotide sequence sandwiched between the two highlighting lines (i.e. from nucleotide position −857 to nucleotide position −691) is represented as SEQ. I.D. No. 1 (see later). This 166 bp nucleotide sequence may be referred to as the "delta" fragment or sequence.

Figure 4:
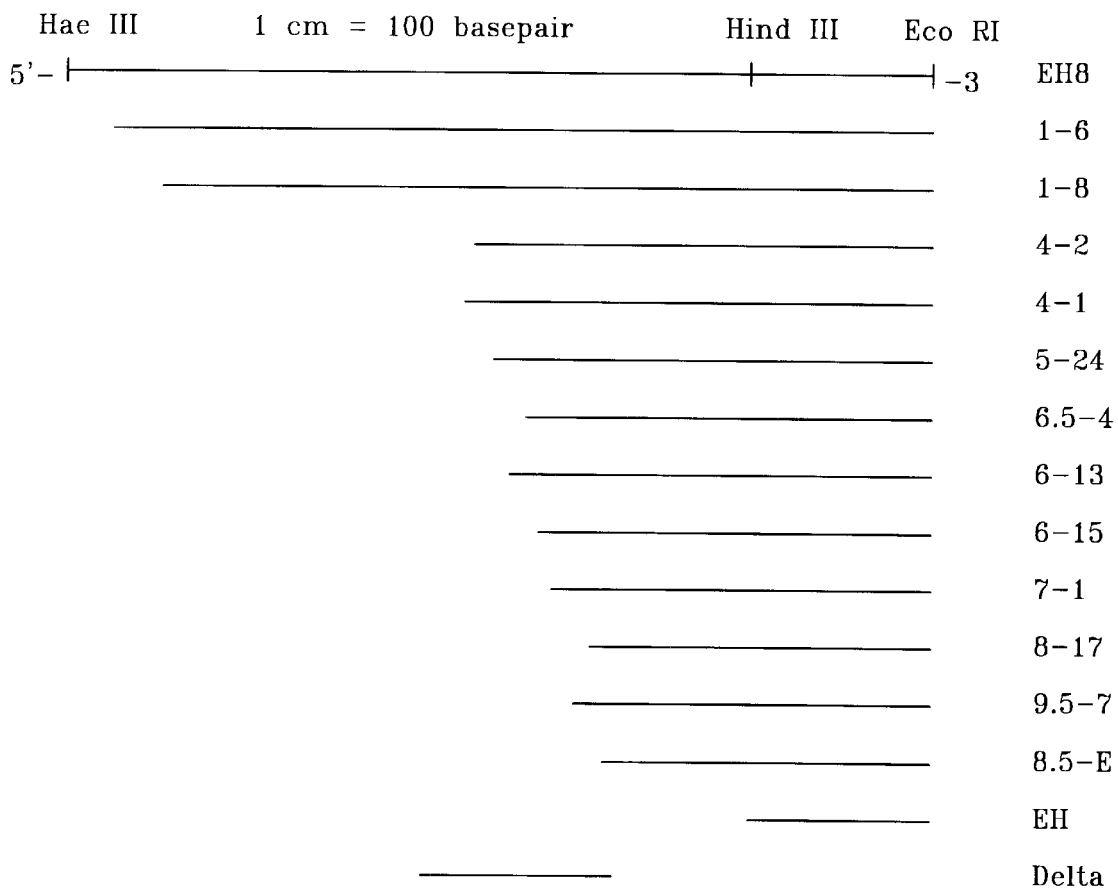
FIG. 4 is a pictorial representation of some deletions made to the sequence of FIG. 2.
Figure 5:
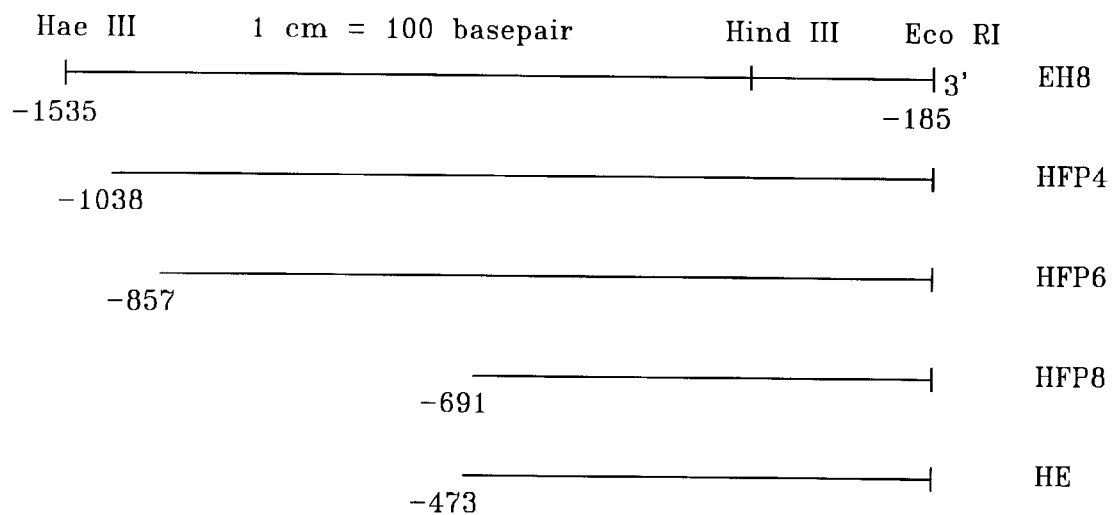
FIG. 5 is a pictorial representation of some deletions made to the sequence of FIG. 2.

FIGS. 4 and 5 represent two deletion series of the alpha-Amy 3 promoter with those of FIG. 5 being used for functional analysis; FIG. 6 shows a series of primer sequences for use with the present invention wherein Uni= T7 primer and Rev=T3 primer.

In further detail, the nucleotide sequence of FIG. 3 is part of the promoter sequence of FIG. 1 (discussed below) and part of the alpha-amylase structural gene, which in turn is part of the sequence of FIG. 8. Part of this nucleotide sequence forms part of the sequences shown in the attached sequence listings. The nucleotide sequence of FIG. 3 is repeated as SEQ ID NOS:17.

FIG. 8 is a pictorial representation of plasmid gPAmy351. The highlighted portion is a EcoR1-SalI fragment isolated from potato (*Solanum tuberosum*)—which is the same as the fragment shown in FIG. 1. The EcoR1-SalI fragment contains the EcoRI 5.5 kb fragment (called subclone Eco 5.5)—which is indicated by the line shown at the bottom of the drawing. The EcoRI 5.5 kb fragment contains the promoter region and part of the 5' untranslated sequence of the structural gene of a potato α-amylase. The following restriction enzyme sites are shown in FIG. 8: E: EcoRI, Ha: HaeIII, Sp: SspI, H: HindIII, P: PvuI, S: SalI. In addition putative CAAT and TATA boxes and the ATG initiation site are shown. Introns are shown as open bars and exons as closed bars.

The EcoRI 5.5 fragment is cloned into a pBluescript M13-plasmid (shown in FIG. 7) or a pBSK-plasmid (also shown in FIG. 7).

For convenience, Chart 1 correlates the sequence references shown in the attached Figures with the sequences shown in the attached Sequence Listings.

CHART 1

| SEQUENCE I.D. No. | FIGURE No./FIGURE REFERENCE |
|---|---|
| 1 | 4/Delta |
| 2 | 4/EH |
| 3 | 4/8.5-E |
| 4 | 4/9.5-7 |
| 5 | 4/8-17 |
| 6 | 4/7-1 |
| 7 | 4/6-15 |
| 8 | 4/6-13 |
| 9 | 4/6.5-4 |
| 10 | 4/5-24 |
| 11 | 4/4-1 |
| 12 | 4/4-2 |
| 13 | 4/1-8 |
| 14 | 4/1-6 |
| 15 | EH8 |
| 16 | -/- |
| 17 | 3 |
| 2 | 5/HE |
| 3 | 5/HFP8 |
| 7 | 5/HFP6 |
| 11 | 5/HFP4 |
| 15 | 5/EH8 |

In the following examples, the following materials and methods were used and followed, respectively.

MATERIALS AND METHODS

Plant Material

Root tissue were harvested from flowering potato (*Solanum tuberosum*, cv. Saturna) plants. The roots were sliced directly into liquid nitrogen and 10–15 g portions were stored at −80° C. until use.

Bacterial Strains

DH5α™ (BRL): F−, enA1, hsdR17($r_k$-, $m_k$+), supE44, thi-1, γ−, recA1, gyrA96, relA1, (argF-lacZYa)U169, σ80dlacZ ΔM15

JM109(1): recA1, endA1, gyrA96, thi, usdR17, supE44, relA1, γ−Δ (lac−proAB), [F', traD36, proAB, LacI$^q$Z ΔMI5]

PLK17 (Stratagene): hsdR-M+, mcrA-, B-, lac-, supE, gal

LE392 (2,3): supE44, supF58, hsdR514, galK2, galT22, metB1, trpR55, lac41

LBA4404: contains the disarmed pTiAch5 plasmid pAL4404 in the streptomycin resistant derivative of the *Agrobacterium tumefaciens* strain Ach5 (4).

| Phages and plasmids | |
|---|---|
| λ EMBL3: | see referenee (5) |
| pBR327: | see referenee (6) |
| pBS+, pBS−: | see referenee (7) |
| pBSK+, pBSK−: | see referenee (7) |
| pBI101, pBI121: | see reference (8, 9) |

Media and Plates

L-Broth (LB) medium:
Per litre: 5 g of yeast extract, 5 g of NZ-amide, 5 g of NaCl, 5 g of bacto-peptone. Autoclave.

LB-plates:
LB medium plus 15 g Bacto agar per litre. Autoclave. Pour into plastic petri dishes (25 ml/dish).

Amp-plates:
As LB-plates plus 35 mg ampicillin per litre after autoclaving.

AXI-plates:
As LB-plates plus 35 mg ampicillin, 120 mg IPTG (isopropylthiogalactoside), 40 mg Xgal (dissolved in dimethylformamide) per litre after autoclaving.
Xgal: 5-bromo-4chloro-3indolyle-β-D-galactoside.

Kan-plates:
As LB-plates plus 50 mg kanamycin per litre after autoclaving.

YMB medium:
Per litre:0.66 g K2HPO4–3H20. 0.2 g MgSO4. 0.1 g NaCl. 10.0 g Mannitol. 0.4 g
Yeast extract. Adjust pH to 7.0. Autoclave.

Liquid MBa medium:
Per litre:4.4 g MS salts (Murashige and Skoog basal salt (10),Sigma). 20 g sucrose. pH is adjusted to 5.7 with NaOH.

Solid MBa medium:
As liquid MBa medium plus 0.8% Difco agar.

MBa co:
As solid MBa medium plus 0.5 mg t-Zeatin (trans-isomer, Sigma) and 2.0 mg 2,4 D (2,4-dichlorophenoxacetic acid, Sigma) per litre.

Solid MBb medium:
As solid MBa medium but instead of 20 g sucrose 30 g sucrose is added per litre.

Water:
The water used in Materials and Methods was always distilled and autoclaved before use.

Isolation of High MW Genomic Potato DNA

In order to gain high molecular weight genomic DNA a procedure essentially as described by Fischer and Goldberg (11), was followed. This include first isolation of nuclei followed by preparation of the nuclear DNA.

10–15 g Saturna root tissue were ground to a fine powder in liquid nitrogen and homogenized in 100 ml H buffer (1×H buffer(11): 100 ml 10×HB, 250 ml 2M sucrose, 10 ml 100 mM PMSF, 1 ml β-mercaptoethanol, 5 ml Triton X-100, 634 ml H$_2$O. Adjust to pH 9.5. Add β-mercaptoethanol just before use. 10×HB: 40 mM spermidine, 10 mM spermine, 0.1 mM Na-EDTA, 0.1 mM Tris, 0.8 mM KCl, adjusted to pH 9.4–9.5 with 10N NaOH. PMSF: phenylmethylsulfonyl fluoride dissolved in ethanol). The resuspended plant material was filtered through a 70 μm nylon filter (Nitex filter, prewetted in 1×H buffer). The resulting filtrate was poured into two centrifuge bottles (Sorvall GSA) and the nuclei were pelleted at 4000 r.p.m for 20 min at 4° C. The supernatant was discarded and the pellets were gently resuspended by adding 20 ml 1×H buffer per tube and then swirling the tubes carefully. The nuclei were pelleted again at 4000 r.p.m. for 20 min at 4° C., the supernatant removed and the pellets resuspended gently in 10 ml 1×H buffer. The supernatant were pooled and 20 ml cold lysis buffer (lysis buffer: 2% Sarcosyl, 0.1M Tris, 0.04M Na$_2$-EDTA) was added dropwise while the solution was stirred gently. Immediately after the last drop of lysis buffer was added, 0.972 g CsCl/ml solution was stirred gently into the solution (the solution should now be at room temperature). The resulting solution was centrifuged for 45 min at 10 krpm, 4° C. The supernatants were carefully removed using a pasteur pipet avoiding any protein debris floating on the top or disturbing the pellets. The volume of the supernatants were determined and 0.2 mg ethidium bromide/ml was added. The DNA solution was gently poured into quickseal polyallomer tubes, which were then sealed. The tubes were centrifuged in a Beckman VTI 65 rotor at 18° C. and 40 k r.p.m. for 38 h. The genomic band was removed under UV-light with a 15–18 gauge needle attached to a 5-ml syringe and poured gently into a 5 ml polyallomer tube.

The tube(s) was then filled with a 1.57 g/ml CsCl solution in 5 mM Tris-Hcl(pH 9.5), 20 mM $Na_2$-EDTA. 75 µl ethidium bromide (5 mg/ml) was added/tube. The tubes were centrifuged in the VTI 65 rotor at 18° C. and 46 k r.p.m. for 17 h. The genomic band was removed under long-wave UV light and the ethidium bromide was extracted with CsCl-saturated isopropanol (7 to 8 times).

The CsCl was removed from the DNA by dialysis in TE-buffer (1×TE: 10 mM Tris-HCl, 1 mM $Na_2$-EDTA pH 8.0) at 4° C. for 18 h with three changes. The high MW genomic potato DNA was not further precipitated and was kept at 4° C.

Construction of a Potato Genomic Library

High MW genomic potato DNA was prepared from cv Saturna roots as described above. The quality of the DNA was tested by restriction enzyme digestion and gel electrophoresis.

The genomic DNA was partially digested with Sau3A and the created fragments (9–23 kb) were inserted into the BamHI site of the λ EMBL3 vector(4). Approximately $1.1 \times 10^6$ independent isolates were plated and amplified to form a permanent library (12). Plaque hybridization was used to screen the library for α-amylase genes.

Screening of the Library

Screening of the potato genomic library was carried out essentially as described by references 13 and 14. The pfu/ml (pfu:plaque forming unit) of the amplified genomic library was determined in duplicate prior to the screening. Infection competent cells (PKL17 or LE392) were prepared by inoculating the cells in 30 ml fresh L-Broth containing 0.2% sucrose and 10 mM $CaCl_2$. The cells were cultivated for 4–5 h at 37° C. before 0.1 vol of cold $CaCl_2$ was added and kept on ice until use. 100 µl phages diluted in phagebuffer to give an appropriate number of pfu (1×phagebuffer: 10 mM Tris-HCl, pH 7.5, 10 mM $MgCl_2$, 20 mM NaCl) were mixed with 25–100 µl freshly made cells (dependent on the actual number of cells) and incubated at 37° C. for 15–20 min. The suspension was mixed with 3 ml warm (42° C.) 0.8–1% top agar containing 10 mM $MgCl_2$ and plated out on dry LB plates.

LB plates of 2×22 cm (dried for 3–4 h at 37° C.) were used for screening of the genomic library. Each plate contained approximately $2 \times 10^5$ plaques, which were mixed with 1 ml of infection competent cells (prepared as above) and incubated for 20 min at 37° C. This mixture was then added to a 25 ml of warm (42–45° C.) 0.3% top agarose with 10 mM $MgCl_2$ and the solution was poured onto a fresh dry LB plate. The large LB plates were incubated (not upside down) overnight at 37° C. Phages from the plaques were transferred to Hybond N filters (Amersham) in duplicates. The plates were placed at 4° C. for 1 to 2 h to prevent the agarose layer from sticking to the filters.

The plates were placed on ice, just before use and they remained on the ice when working with the filters. Two Hybond N filters and a plate were marked for orientation of the filters. The first filter was laid on the plaques for 45 sec; then floated on denaturation buffer (0.5 M NaOH, 1.5 M NaCl) for 7 min, with the phages facing up, then floated on neutralization buffer (0.5 M Tris-HCl (pH 7.4), 3 M NaCl) for 2 times 3 min and finally washed in 2×SSC (1×SSC: 0.15 M NaCl, 0.015 Na-citrate). The filter was air dried and the phage DNA was fixed to the membrane by UV crosslinking. The second filter was laid on the same plate, after the first, for 120 sec and then treated as the first. These filters were used in plaque hybridization following the Hybond N membrane protocol according to suppliers (Amersham) instructions. X-ray film from both the first and second Hybond N membrane was orientated so that the signals from both filters fitted each other.

The positive plaques were cut with a scalpel (1×1 cm blocks) and submerged in 1 ml phagebuffer. The phage containing tubes were stored airtight (parafilm) at 4° C. after 2–3 drops of chloroform has been added. The plaque containing plates (22×22 cm) were stored by placing a piece of soaked (chloroform) filter paper in the lid. The plates were also stored airtight at 4° C. with the plaques facing up. Further purification of the positive plaques were done by plating dilutions of the stock tube (containing the 1×1 cm block) with freshly prepared cells and plate them on round LB plates with 1% warm (42° C.) top-agar and 10 mM $MgCl_2$.

New filter prints were made with Hybond N following the procedure outlined above with the 22×22 cm plates. Plaques which gave positive signal were isolated by sticking the tip of a pasteur pipette though the plate and transfer it to 500 µl phage buffer.

A new series of dilutions were made, plated and the respective filters hybridized until the positive plaques were purified. The phages were stored airtight, at 4° C. either in the 500 µl phagebuffer with 1 drop of chloroform, or as phages isolated from a plate lysate. The plate lysate stock was made as described by (14).

Isolation of Recombinant γ DNA

Large-scale preparations followed the method described in (14), which include banding the recombinant phage DNA on a CsCl gradient. Two versions (A,B) of a small-scale preparation were used as follows:

A) LE392 cells were inoculated in LB with 0.2% maltose and 10 mM $MgCl_2$ and grown O/N at 37° C. The cells were pelleted by centrifugation for 10 min, at 4° C. in a Sorvall centrifuge, and resuspended gently in 1 volume of cold 10 mM $MgSO_4$. The cells were stored at 4° C. until use. Five single plaques from a plate were transferred to 500 µl phagebuffer and allowed to stand for 2–2½ h at 4° C. After votex of the tube 100 µl of the liberated phages were mixed with 200 µl freshly prepared LE392 cells. Alternatively 50–100 µl liberated phages from aplate lysate were mixed with the cells. Phages and cells were incubated for 20 min at 37° C. and then added to a prewarmed (37° C.) 25 ml LB with 20 mM $MgSO_4$ and 30 mM Tris-HCl pH 7.5 and incubated, shaking O/N at 37° C. A further 10 ml prewarmed LB with 20 mM $MgCl_2$ and 30 mM Tris-HCl pH 7.5 was added and the mix incubated for 1–2 h shaking at 37° C. After clear lysis (eventuel a few drops of chloroform was added to help) and the solution was centrifuged at 8000 r.p.m. for 10 min at 4° C. The supernatant was transferred to a new tube and centrifuged again if necessary to remove cell debris.

The recombinant γ DNA was then purified using a Qiagen column following the suppliers instructions (15).

B) The procedure was as under A) until after the first centrifugation of the O/N culture. The supernatant was transferred to a new tube and DNase was added corresponding to 1 µg/ml. The solution was incubated 30 min at 37° C. and then 1 volume of cold 20% PEG, 2 M NaCl mixed in phagebuffer was added and the mixture was incubated 1 h on ice. The phages were pelleted by centrifugation for 20 min, 4° C. at 10 krpm. The PEG pellet was resuspended in 400 µl phagebuffer and transferred to an eppendorf tube. 1 µl of RNasc (10 mg/ml) is added and the tube incubated for 30 min at 37° C. Then 8 µl 0.25 M $Na_2$-EDTA, pH 8.0 and 4 µl 10% SDS were added, the tube was incubated a further 15 min at 68° C. The mixture was allowed to gain room temperature and then an equal phenol saturated with TE-buffer (1×TE: 10 mM Tris pH 7.5, 1 mM $Na_2$-EDTA) was used to extract the DNA. A equal mixture of saturated phenol-chloroform was used to extract the upper aqueous phase and a final chloroform extraction was done. The upper phase was transferred to a new tube and the solution was made 0.3 M Na-acetate and 2–3 vol cold ethanol was added. The precipitation of the DNA was accomplished by storing at O/N at −20° C., centrifuging for 5 min and resuspend the pellet in 50–100 µl TE-buffer. The amount and quality of the recombinant phage DNA was tested by restrictions enzyme digest and agarose (0.8–1%) gel electrophoresis (16).

Preparation of Plasmid DNA

The plasmid preparation was as described in EP-B-0470145. In particular, small scale preparation of plasmid DNA was performed as follows. Bacterial strains harbouring the plasmids were grown overnight in 2 ml L-Broth (LB) medium with ampicillin added (35 µg/ml).

The operations were performed in 1.5 ml Eppendorf tubes and centrifugation was carried out in an Eppendorf centrifuge at 4° C. The cells from the overnight culture were harvested by centrifugation for 2 min., washed with 1 ml 10 mM Tris-HCl (pH 8.5), 50 mM EDTA and centrifuged for 2 min. The pellet was suspended in 150 µl of 15% sucrose, 50 mM Tris-HCl (pH 8.5), 50 mM EDTA by vortexing. 50 µl of 4 mg/ml lysozyme was added and the mixture was incubated for 30 min. at room temperature and 30 min. on ice. 400 µl ice cold H20 was added and the mixture was kept on ice for 5 min, incubated at 70–72° C. for 15 min. and centrifuged for 15 min. To the supernatant was added 75 µl 5.0 M Na-perchlorate and 200 µl isopropanol (the isopropanol was stored at room temperature), and the mixture was centrifuged for 15 min. at 4° C. The pellet was suspended in 300 µl 0.3 M Na-acetate and 2–3 vol. cold ethanol was added. Precipitation was accomplished by storing at either 5 min. at −80° C. or O/N at −20° C., centrifuging for 5 min., drying by vacuum for 2 min. and redissolving the pellet in 20 µl $H_2O$. The yield was 5–10 µg plasmid DNA.

Large scale preparation of plasmid DNA was accomplished by simply scaling up the small scale preparation ten times. Working in 15 ml corex tubes, all the ingredients were scaled up ten times. The centrifugation was carried out in a Sorvall cooling centrifuge at 4° C. Only changes from the above will be mentioned in the following. After incubation at 70–72° C., the centrifugation was for 30 min. at 17,000 rpm. After adding isopropanol and after adding cold ethanol, the centrifugation was for 15 min. at 17,000 rpm. The final plasmid DNA pellet was suspended in $H_2O$ and transferred to an Eppendorf tube and then given a short spin to remove debris. The supernatant was adjusted to 0.3 M Na-acetate and 2–3 vol. cold ethanol were added. The pellet was resuspended in 40 µl $H_2O$. The yield was usually 20–28 µg plasmid DNA.

To obtain very pure plasmid DNA, 200–300 µg of isolated plasmid DNA from the upscaled method were banded on a CsCl gradient. Solid CsCl was mixed with $H_2O$ (1:1 w/v) and 0.2 mg/ml ethidium bromide was added. The solution was poured into a quick-seal polyallomer tube and the plasmid DNA, mixed with solid CsCl (1:1 w/v). The tube was filled, sealed and centrifuged in a Beckman VTI 65 rotor at 15° C., 48,000 rpm for 16–18 hours. The centrifuge was stopped by without using the brake. The banded plasmid DNA was withdrawn from the tubes using a syringe and the ethidium bromide was extracted with CsCl-saturated isopropanol 7–8 times. The CsCl was removed by dialysis in 10 mM Tris-HCl (pH 8.0), 1 mM EDTA for 48 hours with three changes of buffer. The DNA was precipitated by adjusting to 0.3 M Na-acetate and adding 2–3 vol. cold ethanol.

The small scale plasmid preparation from *E. coli* was usually followed by a LiCl precipitation to remove RNA from the DNA solution. The small scale prepared plasmid DNA was dissolved in 100 µl destilled water. 1 vol of SM LiCl was added and the mixture incubated at −20° C. for 30 min followed by centrifugation at 12,000 rpm. for 15 min, 4° C. The supernatant was transferred to a new eppendorf tube and 2 vol TE buffer or water was added. Precipitation with 2.5 vol of 96% ethanol was accomplished by storing either 10 min. at −80° C., or O/N at −20° C. The DNA was precipitated by centrifuging for 15 min. 12,000 rpm ,at 4° C., drying by vacuum for 2 min and redissolving in 18 µl of TE or water.

Restriction Enzyme Digestion

The protocol followed was that outlined in EP-B-0470145. In particular, all restriction endonucleases were from Biolabs, Amersham or Boehringer Mannheim and were used according to the supplier's instructions. 1 unit of enzyme was used to 1 µg of DNA and incubation was for 2 hours.

The buffer was changed in double digestions, by changing the volume or by adding the necessary ingredient according to the enzyme instructions.

Labelling of DNA

A random primed DNA labelling kit (Boehringer Mannheim) was used according to the suppliers instructions. Briefly, 2 µl DNA fragment (25–50 ng) is mixed with 8 µl $H_2O$ and incubated at 95° C. for 10 min to denature the DNA. Spin shortly and place on ice. Then add 1 µl dGTP, DATP and dTTP of each, 2 µl reactionsmix and 5 µl (approx. 50 µCi $dCTP^{32}$). 1 µl Klenow enzyme starts the reaction and the tube is incubated at 37° C. for 30 min. Then place on ice. The labelled DNA fragment was purified using an ELUTIP column (Schleicher & Schuell). The column was prepared by prerunning (gravity) it with 3 ml high salt buffer (1.0 M NaCl, 20 mM Tris-HCl (pH 7,5), 1.0 mM EDTA), followed by 5 ml low salt buffer (0.2 M NaCl, 20 mM Tris-HCl (pH 7,5), 1.0 mM EDTA). 250 µl low salt was added to the labelling tube and the entire solution was laid on the prepared column. Then the column was washed with 2×400 µl low salt followed by 3×200 µl high salt. The eluted radioactive probe was then heat denatured and used in hybridization.

Southern Transfer and Hybridization

The DNA fragments to be transferred were fractionated on non-denaturing agarose gels (14) and transferred to either Hybond™ N or Hybond™ N+, positively charged nylon membrane (Amersham Life Science) by Southern blotting (17,18). Hybridization to the Hybond™ N nylon membranes followed the supplier instructions (18).

Preparation of Vectors

The preparation of vectors was as described in EP-B-0470145 as follows: Vectors (pBS−/+ or pBSK−/+) were digested with one or two restriction enzymes, extracted twice with saturated phenol (the phenol was first mixed with 0.1 M Tris-HCl, then mixed twice with TE-buffer (10 mM Tris-HCl, pH 8, 1 mM $Na_2$-EDTA)) and once with chloroform and precipitated with 0.3 M Na-acetate and 2.5 vol cold ethanol. The pellet was rinsed in 70% cold ethanol and dissolved in $H_2O$, giving a concentration of 25–50 ng/µl. The vectors were tested for background before use (self-ligation with and without T4-DNA-ligase). If necessary the vector was treated with Alkaline phosphatase (Boehringer Mannheim) as described by the supplier. After such a treatment the resulting pellet was resuspended in $H_2O$ to give a final concentration of 10 ng/µl.

Ligation

The phage DNA or plasmid comprising a fragment to be subcloned was digested with one or more restriction enzymes and run in either a 5% acrylamide gel or an appropriate agarose gel. The fragment to be subcloned was isolated from the gel either by electroelution as described in (14) or using a GENECLEAN II Kit (BIO 101 Inc., La Jolla, Calif.) following the suppliers instructions.

Various ratios of fragment to vector were used (from 2:1 to 5:1, based on the number of molecules) in the ligation reaction. 1 µl (10–100 ng) of a solution containing the vector was combined with the fragment, 1 µl of T4-ligation buffer (10×(20 mM Tris-HCl, pH 7.6, 10 mM $MgCl_2$, 0.6 mM ATP, 10 mM dithitheitol)) and 1 µl of T4-DNA ligase (Boehringer Mannheim) were added to a mixture of fragment and vector to a total volume of 10 µl. The reaction was incubated at 15° C. O/N if the ligated DNA fragments had sticky ends.

If the DNA had blunt ends, the incubation was at room temperature for 1 hour. The ligation mixture was stored at −20° C. if not used immediately, usually 5 µl of the ligation mix was used for transformation.

DNA fragments treated with a DNA blunting kit (see "subcloning and sequencing") were ligated following the DNA blunting kit's protocol (Amersham).

Preparation of Competent E. coli Cells and Transformation

This was done according to the protocols laid down in EP-B-0470145 as follows:

JM109 cells (or DH5α) were inoculated in 4 ml L-Broth made to 10 mM $MgSO_4$ and 10 mM $MgCl_2$. The cells were grown O/N at 37° C. 1 ml of the O/N culture was added to 40 ml prewarmed (37° C.) LB medium (with 10 mM $MgSO_4$ and 10 mM $MgCl_2$). The culture was shaken at 250–275 rpm for 1 to 2 h until the $OD_{450}$ reached 0.8–0.9. The cells were harvested by centrifugation at 5000 rpm for 10 min at 4° C. The pellet was gently resuspended in 30 ml of cold 0.1 M $CaCl_2$, another centrifugation pelleted the cells again and they were then resuspended in 15 ml of cold 0.1 M $CaCl_2$. The suspension was placed on ice for 20 min followed by a centrifugation as before. Finally, the cells were gently resuspended in 3 ml of cold 0.1 M $CaCl_2$ and placed on ice for at least 1 h before they were ready to use for transformation (19).

5 µl of ligation mix was combined with 95 µl of cold sterile TCM (10 mM Tris-HCl, pH 7.5, 10 mM $CaCl_2$, 10 mM $MgCl_2$, and 0.2 ml of the competent cells. The mixture was allowed to stand for at least 40 min on ice, then 5 min at 37° C. (or 2 min at 42° C.). The solution was transferred to 0.8 ml of L-Broth, 10 mM MgSO4, 10 mM $MgCl_2$, and incubated for 45 min at 37° C. and then plated out on 5 AXI or other plates (as e.g. Amp-plates) at 0.2 ml/plate.

The plates were allowed to stand 10 min before being inverted and incubated O/N at 37° C. They were stored in plastic bags upside down at 4° C.

ExoIII/Mung Bean Nuclease Deletions

A deletion series of a subcloned larger genomic fragment was performed using a ExoIII/Mung Bean Deletion Kit (Stratagene). The subclone selected for the deletion series was purified by banding twice on a CsCl gradient (see "Preparation of plasmid DNA") to obtain high amounts of supercolied plasmid DNA. Generation of the deletions was performed using the ExoIII/Mung Bean Deletion kit following the suppliers instructions. The temperature during the ExoIII treatment was 23° C. since at that temperature approximately 125 bp should be removed per min.

Purification of Primers Following Synthesis on a DNA Synthesizer

The primer was synthesized on a polystyrene support column (Applied Biosystems, 393 DNAJ/RNA Synthesizer) and was eluted from the column with $NH_4OH$. The column was broken open and 1.5 ml $NH_4OH$ was added to the polystyrene material in a small glass tube. The mixture was incubated at 85° C. for 1 hour followed by 5 min on ice. The supernatant containing the single stranded DNA was transferred to eppendorf tubes, and the $NH_4OH$ was evaporated in a vacuum centrifuge for at least 3 h. Pellet was resuspended in 200 µl destilled water and precipitated with 550 µl ethanol and 20 µl sodium acetate. The pellet was resuspended in 200 µl water and precipitation with ethanol and sodium acetate was repeated. Finally the pellet was resuspended in 100–200 µl destilled water and the $OD_{260}$ was measured by a Gene Quant RNA/DNA calculator (Pharmacia) of single stranded DNA is calculated. An $OD_{260}$ of 1 corresponds approx. to 33 µg/ml single stranded DNA.

Subcloning and Sequencing

Purified γ DNA was digested with appropriate restrictions enzymes and the generated fragments were isolated from agarose gels using a GeneClean Kit (BIO 101 Inc., La Jolla, Calif.) according to the suppliers instructions.

Genomic DNA fragments (or fragments obtained from plasmids) were ligated into the polylinker region of the BlueScribe vector pBS−/+ (or pBSK−/+, Stratagene). After transforming an E. coli strain with the ligated plasmid the recombinant subclones could be selected by plating on AXI plates (they will be white and the nonrecombinant clones will be blue when the vector is a pBlueScript plasmid,(107)).

Plasmid DNA from putative subclones were digested with appropriate restriction enzymes, subjected to gelelctrophoresis and after Southern blotting, hybridized with an appropriate labelled DNA probe, to verify the origin of the inserted fragment.

The generated pBS genomic DNA subclones were then sequenced according to the plasmid preparation protocol outlined in EP-B-0470145. In this regard, the plasmid (double stranded template) to be sequenced was purified by the plasmid small scale preparation method. The DNA was denatured in 0.2 M NaOH (5 min at room temperature) the mixture was neutralised by adding 0.4 vol of 5 M ammonium acetate (pH 7.5) and then precipitated with 4 vol. of cold ethanol (5 min at −80° C.). The pellet was rinsed with 70° C. cold ethanol and resuspended in 10 µl $H_2O$.

For subcloning of DNA fragments generated by using an ExoIII/Mung Bean Nuclease kit,the fragments were either blunted first or digested with a restriction enzyme, following by blunting.

The blunting of the DNA with an unknown end structure (after the ExoIII/Mung Bean treatment) or with cohesive ends was accomplished by using a DNA blunting kit (Amersham) following the suppliers instructions. The generated ligated (see "Ligation") deletions plasmids were transformed into DH5α competent cells and white colonies, selected on AXI plates, were analysed for their insert by restriction enzyme digestion and further, by sequencing.

Sequencing was accomplished with a Sequenase™ DNA Sequencing Kit from United States Biochemical Corp., following the sequencing Protocol enclosed in the kit (Sequenase™ :Step by Step Protocols for DNA sequencing with Sequenase, 3rd Edition, United States Biochemical Corporation PO Box 22400 Cleveland Ohio 44122). The following modifications were however made to the suggested protocol. Instead of adding DTT, Labelling mix and $^{35}$SdATP to the annealed DNA mix, 4 ml of $^{35}$Sequetide (DuPont) was added.

In addition to T3 and T7 primers (Stratagene) a whole range of other primers generated on a DNA synthesizer (Applied Biosystems, 392 DNA/RNA Synthesizer) were used. 0.5 pmol of primer was used to sequence 1 pmol of plasmid.

The primer sequences are shown in the FIG. 6.

The sequencing reaction were subjected to electrophoresis on 6% or 8% denaturing polyacrylamide gels for 1 to 4 hours at 40 W, then dried by a gel drier and autoradiographed for 3–48 hours at room temperature.

The denaturing sequencing gels were made from pre-mixed polyacrylamide solutions, Gel-Mix 6 and Gel-Mix 8 (GIBCO BRL, Life technologies, Inc) according to the manufacturers instructions.

Preparation of Competent Agrobacterium Cells and Transformation

The LBA 4404 strain was kept at YMB plates (pH 7.0) containing 100 mg/ml of rifampicin (Sigma) and 500 mg/ml of streptomycin (Sigma). 2.5 ml of LB medium (pH 7.4) was inoculated with the bacteria. The suspension was left growing for 24 hours at 28° C. in an incubation shaker at 300–340 rpm. The suspension was then diluted 1:9 with LB and incubated for another 2–3 hours at 28° C. and 300–340 rpm.

When OD was 0.5–1, 25 ml aliquots of the cells were harvested in 50 ml tubes in a cooling centrifuge at 10.000 rpm, 5 min, 4° C. The tubes were placed on ice and the pellet resuspended in 0.5 ml of 20 mM $CaCl_2$. 0.1 ml aliquots of the resuspended cells were quickly frozen in 1 ml cryotubes in liquid nitrogen and stored at −80° C.

Transformation was accomplished using the freeze-thaw method (20) as follows:

A 0.1 ml aliquot of $CaCl_2$ competent LBA 4404 cells was thawed on ice and added 1 $\mu$g of plasmid DNA. The mixture was incubated at 37° C. for 5 min. and added 1 ml LB (pH 7.4). Incubation at room temperature with shaking (100 rpm.) for 4 hours was followed by a quick spin at 10.000 rpm, 4° C. for 30 sec. The pellet was resuspended in 100 $\mu$l LB and plated on a YMB plates containing 50 mg/l of kanamycin (Sigma).

The plates were incubated for 48 hours at 28° C. or until the colonies had a suitable size.

This was the first round of selection. Only bacteria transformed with a plasmid containing the NPT II gene conferring kanamycin resistance is able to survive on the kanamycin plate.

For the second round of selection six of the obtained colonies were transferred to a YMB plate containing 100 mg/l of rifampicin, 500 mg/l of streptomycin and 50 mg/l of kanamycin. LBA 4404 is resistant to rifampicin and streptomycin and the plasmid confers resistance to kanamycin. The plates were incubated at 28° C. until the colonies reached a suitable size (approx. 4–5 days).

The colonies were tested for their plasmid content. Plasmid preparations of the colonies were generated and the DNA was digested with appropriate restriction enzymes and run on a 1% agarose gel to ensure that the plasmid and the inserted fragment had the right size. The digested DNA was blotted onto a Hybond N+ membrane and hybridised with an appropriate radioactively labelled probe (a fragment of the plasmid DNA or insert).

Storage of the transformed LBA 4404 was at −80° C. 2 ml LB medium containing 100 mg/l of rifampicin, 500 mg/l of streptomycin and 50 mg/l of kanamycin was inoculated with bacteria and incubated at 28° C. for 48 hours with shaking (300–340 rpm). The suspension was diluted 1:1 with sterile 35% glycerol and aliquoted into cryotubes, 800 $\mu$l per tube and stored at −80° C.

Transformation of Potato

A culture of the transformed LBA 4404 bacteria were made by inoculating 2 ml of YMB (pH 7.0) with the bacteria and incubating at 28° C. for 24 hours. The suspension was diluted 1:10 and incubated for another 18 hours. The bacteria was centrifuged at 10.000 rph, 4° C. for 10 min. and the pellet rinsed twice with 2.5 ml of 2 mM magnesium sulfate, before resuspension in liquid MBa to an OD660 nm of 0.5.

The potato plant material used for transformation was maintained in vitro at MBa medium added 2 $\mu$M STS (21,22). By multiplication top shoots as well as nodes were applied, if the leaves were big they were removed. 5 shoots per container with 80 ml medium was left growing at 25° C. and 30–35 days after subcultivation the nodes could be used for transformation.

The stems of micropropagated plants were cut just above and beneath the node so that only the internodes are used, these may possibly be divided so that the explants are approx. 4 mm long. The explants were floated in the bacterial suspension for 30 min. and blotted dry on a filter paper and transferred to co-cultivation plates (MBa co). The explants were covered with filter paper moistened in liquid MBa, and the plates were covered with cloth for 3 days and left at 25° C. The explants were then washed in liquid MBa containing 800 mg/l. 2 explants per ml were shaken for 18 hours, then blotted dry and transferred to selection medium.

The selection medium was solid MBb added 50 mg kanamycin, 800 mg carbenicillin (Duchefa), 0.1 mg $GA_3$ (Gibberellic Acid,Sigma) and 1 mg t-Zeatin per litre. The carbenicillin was added to kill any remaining, 4 grobacteria.

The explants were subcultivated every 3 weeks.

Regeneration of Whole Potato Plants

Shoots from the explants which by subcultivation was more than 1 cm were harvested and transferred to a solid MBa medium containing 400 mg/l of carbenicillin, 2 $\mu$M STS and 0.5 mg/l t-Zeatin. After approx. 2 weeks the shoots were transferred to root-formation medium, that is solid MBa with 2 $\mu$M STS added. A 5 $\mu$M stock of STS was made from 0.19 g of $Na_2S_2O_3$—$5H_2O$ and 10.19 mg of $AgNO_3$ dissolved in 7 ml of water and sterilised by filtration.

After approx. 2 weeks the shoots had rooted and were ready for planting in soil.

The plantlets were rinsed in lukewarm water to remove residues of media and planted in small pots with TKS 2 instant sphagnum (Flora Gard, Germany). The plantlets were kept moist during the planting and watered after. The pots were placed in a "tent" of plastic with 100% humidity and 21–23° C., until the plantlets were rooted in the soil. Then the tent was removed and the plants watered regularly.

After 4 weeks of growth the plants were potted into large pots (diameter 27 cm) and transferred to a growth chamber with 16 hours day 22° C. and 8 hour night 15° C. When the plants had wiltered down, the tubers were harvested.

Generation of Microtubers from in vitro Propagated Potato Plants.

From an in vitro propagated plant or a selected shoot a node was cut of 5 mm under and 2 mm over the node. The leaf was removed and the explant was placed on a solid growth medium. The medium contained per litre: 4.4 g Murashige and Skoog (MS,(10)) basal salts (Sigma), 60 g sucrose, 2 mg BAP (6-Benzyl-aminopurine, Sigma), 2 g Gelrite (Scott Laboratories, Inc., Carson, Calif.). The explants were incubated for 7 days at 20° C., with 16 h light/ 8 h dark. The plates were then wrapped in aluminium foil and kept in the dark at 20° C. for 21–28 days. Then microtubers could be harvested, one per explant.

Sprouts from microtubers were generated from the microtubers by cutting the tubers in two halves (from top to bottom). They were then placed on solid MBa medium and incubated in the dark for 7 days at 25° C. and the newly developed sprouts could be GUS analysed.

Histochemical Localisation of Beta-glucuronidase (GUS) Activity

The tissue was cut in small sections with a razor blade and placed in X-gluc (X-gluc: 5-bromo-4-chloro-3-indolyl-β-glucoronide) is a solution of 50 mg X-gluc dissolved in a buffer with: 0.1 M $NaPO_4$ (pH 7.0), 1 mM $K_3(Fe(CN)6)$, 0.1 mM $K_4(Fe(CN)6)$—$3H_2O$, 10 mM $Na_2EDTA$ and 3% sucrose (23)) solution to cover the section.

Micro tubers were halved, pot grown tubers were sliced into thin slices, leaves were cut into pieces approx. 0.5 $cm^2$ and stem tissue was cut into slices approx. 1 mm thick.

The sections were incubated in X-gluc for 2–12 hours at 37° C. Care was taken to prevent evaporation. The X-gluc was removed and 96% ethanol was added to the tissue sections to extract chlorophyll and other pigments. Incubation in ethanol was overnight at 5° C. and the following day the tissue was transferred to a 2% sucrose solution and after approx. 1 hour examined in a dissection scope.

Isolation of α-amylase Genomic Clones

Several cDNA clones encoding α-amylase from potato (*Solanum tuberosum*) had previously been isolated (described in EP-B-0470145). A PstI-SalI fragment from the plasmid pAmyZ3 (EP-B-0470145) encoding a partial α-amylase was used as probe (see "DNA labelling" in Materials and Methods) to screen the genomic potato γ DNA library (see "Construction of a potato genomic library" in Materials and Methods). Screening of approx. $1.6 \times 10^6$ phages was carried out as described in Materials and Methods. Two positive clones were isolated, gPAmy351 and gPAmy331 by three rounds of plaque purifications.

One clone (gPAmy331) was found to be unstable during isolation of the γ DNA (see the method in Materials and Methods), then only the gPAmy351 clone was analyzed in details.

A restriction enzyme map of the insert (insert size approx. 22 kb) is shown in FIG. 1.

Mapping of the α-amylase encoding part of the genomic sequence was done by Southern transfer of various digests of the clone, followed by hybridization with the PstI-SalI fragment of pAmyZ3. gPAmy351 contain the whole promoter region of the α-amylase gene and in addition 1270 bp of the structural gene. This covers the sequences encoding 142 amino acids corresponding to approx. ⅓ of the total amino acid sequence encoded by the Amy¾ type potato α-amylase (407 amino acids, see EP-B-0470145).

Subcloning of the Genomic Fragment Containing the α-amylase Promoter

The EcoR1 fragment of approximately 5.5 kb, indicated by an asterisk in FIG. 1, was subcloned from the gPAmy351 genomic clone into a dephosphorylated EcoRI site of a pBS-vector (see Materials and Methods).

This subclone was named Eco 5.5 and it contains the ATG initiation codon and sequences upstream of it (see the next paragraph for a more detailed description of the sequence). These upstream sequences will in the following be referred to as the α-Amy 3 promoter.

A large scale plasmid preparation of the Eco 5.5 plasmid was digested with EcoRI and HaeIII, this creates a 1350 bp fragment which includes the ATG initiation codon as well as putative CAAT and TATA boxes.

As shown by others (eg see 24–31) it is often the sequence region counting from the ATG initiation codon and approx 1000–1500 bp upstream that includes the entire promoter, enough to mediate transcription of the gene at the right time and place. The EcoRI-HaeIII fragment was subcloned into a pBSK-vector, digested with EcoRI and SmaI and dephosphorylated by Alkaline phosphatase (see Materials and Methods). This subclone was named EH8 and the genomic potato fragment it carries was chosen for functional analysis. The identity of the insert in the EH8 plasmid was verified by sequencing with T3 and T7 primers (see FIG. 2B and Materials and Methods).

Sequencing of the α-amylase Promoter

Approximately 2900 bp of the insert in gPAmy351 (FIG. 1) was sequenced by subcloning various fragments and using the primers shown in FIG. 6 (see Materials and Methods). This covers 1734 bp upstream of the initiation (ATG) codon and 1440 downstream. The sequence map of the region upstream of the ATG initiation codon is shown in FIG. 2A and the DNA sequence is shown in FIG. 3. This sequence is located near the 3' end of the gPAmy351 insert (see FIG. 1) covering part of the Eco 5.5 kb fragment and the HindIII and EcoRI sites upstream of the initiation codon, and thereby including the HaeIII-EcoRI (EH) fragment chosen for the functional analysis.

The α-Amy 3 promoter sequences from the ATG (A in position +1) codon and upstream to position -1734 (see FIG. 3) were compared with the (EMBL) database of published plant sequences (using the PC-gene program from IntelliGenetics, Inc., California) and also compared with sequences of all organisms. There were no sequences with significant overall homology to the α-Amy 3 promoter. A TATA-box is located at position -365.

Comparing the α-Amy 3 promoter with published DNA binding sites suggested a CAP site to be localized 21 bp downstream of the TATA box (position -344) and two CAAT boxes, one at position -468, which is 103 bp upstream of the TATA box, and 124 bp upstream of the CAP site, and the other at position -557, 192 bp upstream of the TATA box and 213 bp upstream of the CAP site.

The positions of the CAP site, TATA- and CCAAT-box correspond well to the positions found in other eukaryotic polymerase II promoters (32–33)

α-amylase Promoter Deletions

Plasmid from a large scale preparation of the EH8 subclone was banded twice on a CsCl gradient (see Materials and Methods) to obtain pure supercoiled DNA. Running a sample of the plasmid DNA on an agarose gel showed that at least 85% of the preparation was supercoiled. Then the EH8 plasmid was digested with Bst XI which creates a 3' overhang and with BamHI which creates a 5' overhang end, and care was taken to be sure that the digests were complete. An ExoIII/Mung Bean treatment was done as described in Materials and Methods, and aliquots were taken at 0, 1, 2, 3, 4, 5, 6, 6.5, 7, 7.5, 8, 8.5, 9, 9.5, 10 and 10.5 min. The different mixtures now containing the nested deletions of the EH8 plasmid were used directly in ligation and transformation as explained in Materials and Methods. A whole range of deletion subclones were obtained, these are shown in FIG. 4. They were all sequenced with the T3 and T7 primers (see FIG. 8) to locate their 5' end in proportion to the α-Amy 3 promoter. The individual start positions are shown in FIG. 2A where the arrows indicate the start and extent of the sequence reactions of the deleted subclones.

Three of the nested deletion subclones were chosen for functional analysis, these were 4-1, 6-15 and 8.5-E (indicated with an asterisk in FIG. 2B).

A large scale plasmid preparation was generated from each of the selected deletions cloned (4-1, 6-15 and 8.5-E) and from the EH8 clone. These were then digested with SacI which cuts in the polylinker of pBSK- and the site blunted (see Materials and Methods) before they were digested with SalI, which cuts on the opposite site of the promoter insert.

A pBI101 plasmid (see Materials and Methods) containing a promotorless β-glucuronidase (GUS) gene was completely digested with HindIII and the HindIII sites blunted as described in Materials and Methods. Afterwards the open plasmid was digested with SalI thereby creating a pBI101 HindIII$^{Blunt}$/SalI vector.

Subcloning and Transformation

The Sac I Blunt/Sal I fragments obtained from the 4-1, 6-15, 8.5-E and EH8 clones were then subcloned into the pBI101 HindIII$^{Blunt}$/SalI vector and the ligated plasmids transformed into the Agrobacterium strain LBA4404 (see Materials and Methods). The colonies obtained were tested using the restriction enzymes PstI and SalI which cut on either side of the inserted fragment. Clones which contained an insert of the right size were then analysed by sequencing with a primer named #589 (see FIG. 6). The #589 primer primes within the GUS gene of pBI101 and allows the reading of sequences upstream of the promoterless GUS gene thereby covering the inserted promoter deletions.

The pBI101 plasmids containing the selected promoter deletions were named EH, HFP4, HFP6 and HFP8.

In addition, a Southern transfer of the PstI and SalI digested plasmids was hybridized with a labelled insert from the EH8 clone which contained the largest fragment of the α-Amy 3 promoter region, to verify the origin of the inserts.

To produce a smaller fragment than the one covered by 4-1, 6-15, 8.5-E or EH8, another subclone was created, the HE subclone. This was accomplished by digesting the EH8 subclone with EcoRI and blunt end the EcoRI site followed by a digest of HindIII and then isolate the 288 bp fragment containing 3' end promoter sequences (see FIG. 2B for position of the HE fragment). For subcloning this HindIII/EcoRI$^{Blunt}$ fragment into a pBI101 vector digested with SmaI and HindIII was used in the ligation reaction. The resulting plasmid is called HE and was transformed into the Agrobacterium strain LBA4404 (see Materials and Methods). The colonies obtained on kanamycin plates were tested by digesting purified plasmid with the restriction enzymes HindIII and SnaBI. Plasmids from selected colonies were subjected to sequence analysis with the #589 primer as explained above.

In total, five deletions of the α-Amy 3 promoter constructs have been made as explained in the preceding sections. They cover 1350 bp (EH8), 853 bp (HFP4), 672 bp (HFP6), 506 bp (HFP8) and 288 bp (HE) of the sequences upstream of the EcoRI site 5' to the ATG codon (see FIG. 2 and FIG. 5). They were cloned in front of the promoterless GUS gene of the pBI101 vector (see Materials and Methods).

Transformation of Potato with the Promoter Constructs

Six LBA4404 colonies containing the 5 deletion constructs and the pBI101, were selected and used for transformation of Saturna stem tissue as described in Materials and Methods.

As a negative control some Saturna explants were incubated with nontransformed LBA4404 bacteria and nontransformed shoots obtained from selection plates without kanamycin. As a positive control some Saturna explants were incubated with LBA4404 previously transformed with the pBI121 plasmid. pBI121 contain a GUS cassette controlled by the Cauliflower mosaic virus (CaMV) 35S promoter which is constitutively expressed in most plant tissues (34–38).

All regenerated shoots after the first (22 days) and second (49 days) harvest were discarded. After 68 days were 40 shoots from each deletion construct, 10 shoot from the negative control and 15 shoots from the positive control harvested and transferred to root induction medium (see Materials and Methods). Each shoots represents, putatively, an individual transformation event and will in the following be referred to as lines. Each line, if the plant is transformed, represent an independent transformation event.

Expression of GUS in Leaves of Putatively Transformed Lines

Leaves from the regenerated lines were all GUS tested after root formation. An expression analysis of the α-amylase genes of the present invention revealed that the α-amylase type ¾ is expressed in tuber-, sprout-, stem- and root tissue but no expression was found in leaves.

The GUS testing of leaves, from the putatively transformed deletion lines, from the lines transformed with the pBI101 plasmid, and from the nontransformed control lines, revealed that there were no GUS activity in any of these. In contrast, GUS testing of plants transformed with the positive control plasmid pBI121 showed GUS expression in the leaves in nearly all the plants (see table 1).

Expression of GUS in Microtubers and Sprouts

Micro tubers from the lines described above were generated as described in Materials and Methods. These microtubers were examined for their GUS activity and lines containing the EH8, HFP4 and HFP6 deletion constructs showed positive GUS staining. Again the pBI121 control lines gave GUS positive microtubers while the lines containing the pBI101 plasmid showed negative microtubers. Also non-transformed lines microtubers showed no GUS activity as well as lines transformed with the deletion constructs HFP8 and HE.

Sprouts generated from microtubers (see Materials and Methods) were also GUS analysed and only the lines transformed with the pBI121 (positive control) showed GUS activity.

The results are summarized in Table 1, shown below.

TABLE 1

| | | | Expression of GUS | | | | |
|---|---|---|---|---|---|---|---|
| Plants TD with: | Leaf of explant | Micro-tuber | Leaf-like of EP | Stem-like of EP | Sprout | Leaf of pot grown plant | Pot grown tubers |
| EH | 0 (36)* | 7 (36) | 0 (15) | 0 (15) | 0 (33) | 0 (40) | 16 (22) |
| HFP4 | 0 (36) | 2 (36) | 0 (15) | 0 (15) | 0 (31) | 0 (40) | 15 (24) |

TABLE 1-continued

Expression of GUS

| Plants TD with: | Leaf of explant | Micro-tuber | Leaf-like of EP | Stem-like of EP | Sprout | Leaf of pot grown plant | Pot grown tubers |
|---|---|---|---|---|---|---|---|
| HFP6 | 0 (32) | 5 (32) | 0 (15) | 0 (15) | 0 (26) | 0 (40) | 10 (26) |
| HFPS | 0 (30) | 0 (30) | 0 (10) | 0 (10) | 0 (15) | 0 (40) | 0 (21) |
| HE | 0 (34) | 0 (34) | 0 (14) | 0 (14) | 0 (27) | 0 (40) | 0 (23) |
| pBI 101 | 0 (36) | 0 (36) | 0 (36) | 0 (36) | 0 (36) | 0 (40) | 0 (24) |
| pBI 121 | 10 (15) | 10 (15) | 10 (10) | 10 (10) | 6 (6) | 10 (15) | 5 (5) |
| Non TD plants | 0 (15) | 0 (9) | — | — | 0 (9) | 0 (15) | 0 (12) |

*The numbers in brackets are the total numbers of lines tested.
(TD = transformed; EP = Explant)

Expression of GUS in Other Parts of the Planlets

When microtubers are generated they are formed at the end of the stem explant. On top of the explant most often two leaf-like structures are formed. These stem-like explants and the leaf-like tops were examined for GUS activity. As summarized in table 1, none of the deletions containing lines showed any GUS activity in either the stem-or leaf-like tissues of the explants.

All the pBI121 lines which showed GUS activity in their microtuber also had GUS activity in the stem- and leaf-like structures of the explant.

Expression of GUS in Leaves, Roots, Stems and Tubers of Pot Grown Lines

The regenerated potato lines were also grown in pots in a growth chamber (at 22° C., 16 h light and 15° C., 8 h dark) and leaves, roots, stems and tubers were GUS analysed. None of the plant lines, except the control lines containing the pBI121 construction, showed GUS activity in the leaves as summarized in Table 1 and Table 2.

Investigation of GUS expression in tubers harvested from the pot grown plants, repeated the pattern already seen with the lines tested in the microtubers.

The plants carrying one of three constructs EH8, HFP4 and HFP6 showed GUS activity in the tubers while the plants carrying the HFP8, HE or pBI101 constructs showed no GUS activity in their tubers.

Again the plants carrying the pBI121 construct had GUS activity in their pot grown tubers as expected.

A GUS analysis of the lines listed in table 2 (except for the positive control plants carrying pBI121) showed that there were no GUS activity found in root, stem or leaf tissues even though the lines EH8, HFP4 and HFP6 containing lines clearly showed GUS activity in both microtuber and pot grown tubers.

TABLE 2

Expression of GUS in pot grown potatoes

| Line No. | Construct | Stem | Leaf | Root | Tuber |
|---|---|---|---|---|---|
| Saturna | | | | | |
| control | — | 0 | 0 | 0 | 0 |
| K702-15.2 | EH8 | 0 | 0 | 0 | + |
| K702-41.6 | | 0 | 0 | 0 | + |
| K702-47.3 | | 0 | 0 | 0 | + |
| K702-28.2 | | 0 | 0 | 0 | + |
| K699-2.2 | HFP4 | 0 | 0 | 0 | + |
| K699-31.5 | | 0 | 0 | 0 | + |
| K699-44.2 | | 0 | 0 | 0 | + |
| K700-1.5 | HFP6 | 0 | 0 | 0 | + |
| K700-24.3 | | 0 | 0 | 0 | + |

TABLE 2-continued

Expression of GUS in pot grown potatoes

| Line No. | Construct | Stem | Leaf | Root | Tuber |
|---|---|---|---|---|---|
| K700-38.2 | | 0 | 0 | 0 | + |
| K703-44.6 | HFP8 | 0 | 0 | 0 | 0 |
| K701-5.3 | HE | 0 | 0 | 0 | 0 |
| K701-15.2 | | 0 | 0 | 0 | 0 |
| K701-18.2 | | 0 | 0 | 0 | 0 |
| K701-16.2 | | 0 | 0 | 0 | 0 |
| K701-49.2 | | 0 | 0 | 0 | 0 |
| K661-10.4 | pBI121 | + | + | + | + |
| K661-15.3 | | + | + | + | + |

In conclusion, it is clear that none of the α-Amy 3 promoter deletion constructs covering 1534 bp upstream of the ATG initiation codon leads to expression of an otherwise promoterless GUS gene in leaves of plantlets or pot grown plants, in leaf-and stem-like tissues of microtuber explants or in roots and stems of pot grown plants.

GUS expression is only found in microtubers and pot grown tubers clearly showing that this α-Amy 3 promoter contains a tuber specific element clearly separable from the stem, sprout and root expressing element(s) situated upstream of the EH8 deletions 5' end.

In addition this invention also shows that the tuber specific element is situated near and upstream of the HFPS deletions 5' end and is covered by the delta sequence. This invention also show that the stem, sprout and root expressing element(s) is positioned upstream of the 5' end of EH8, since neither EH8, HFP4, HFP6, HFP8 nor EH constructs gave GUS expression in these tissues.

It is therefore concluded that the elements directing root-specific, stem-specific and sprout-specific expression are located far upstream in the 351 promoter.

The applicability of the promoters is widespread. With the promoters it is possible to direct the expression of proteins into different tissues in the potato plant. It is even possible to direct the expression of proteins into different tissues in othe r dicot plants.

pJK4

The potato α-amylase encoding sequences originate from plasmid pAmyZ4 (see detailed description in EP-B-0470145). Briefly pAmyZ4 encodes a 407 amino acid long potato α-amylase precursor and in addition contains 149 bp 5' and 201 bp 3' untranslated sequences positioned in the EcoRI site of the plasmid pBSK-'s polylinker.

Figure 9:
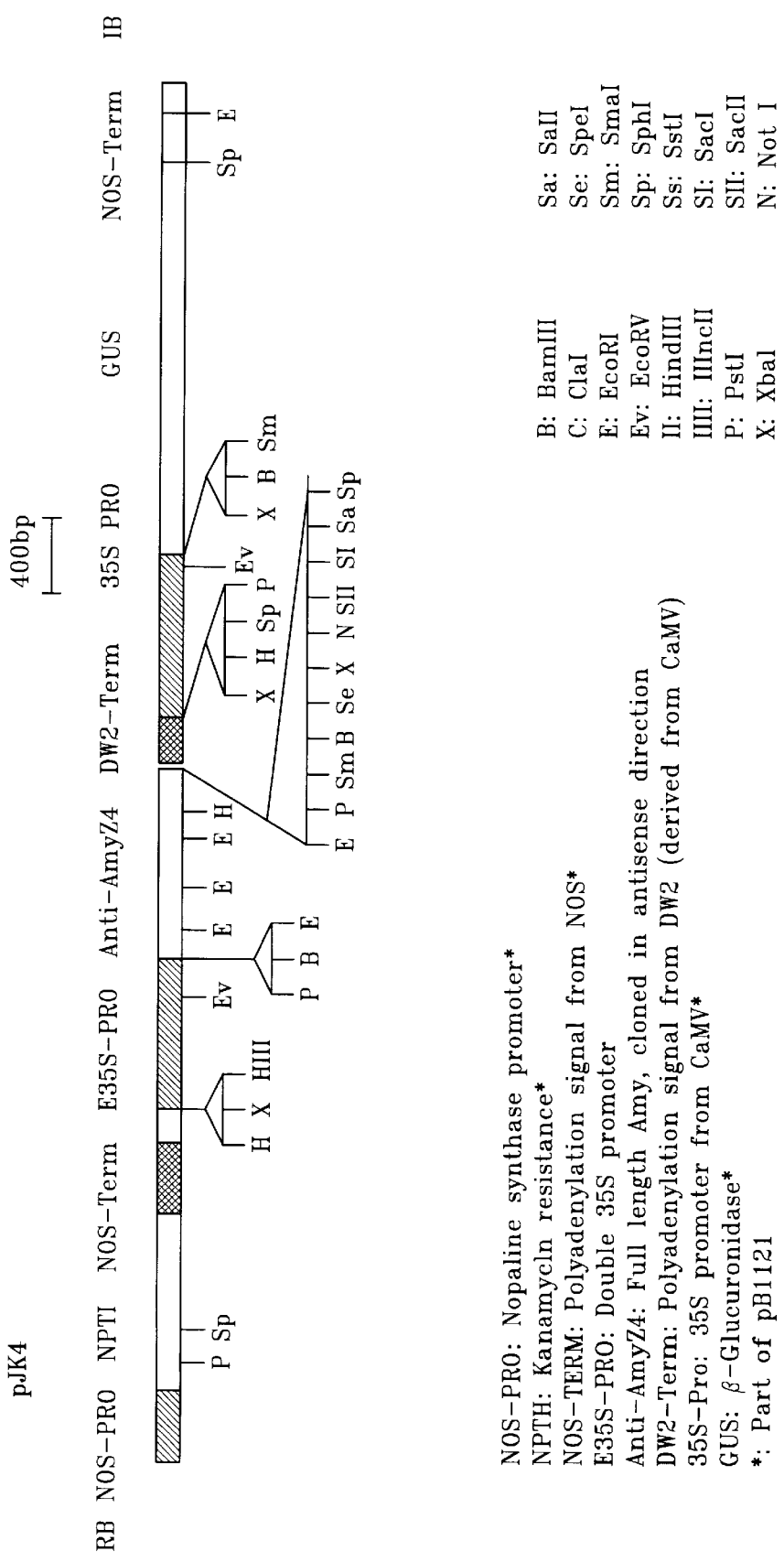
FIG. 9 is a restriction map of pJK4.
Figure 10:
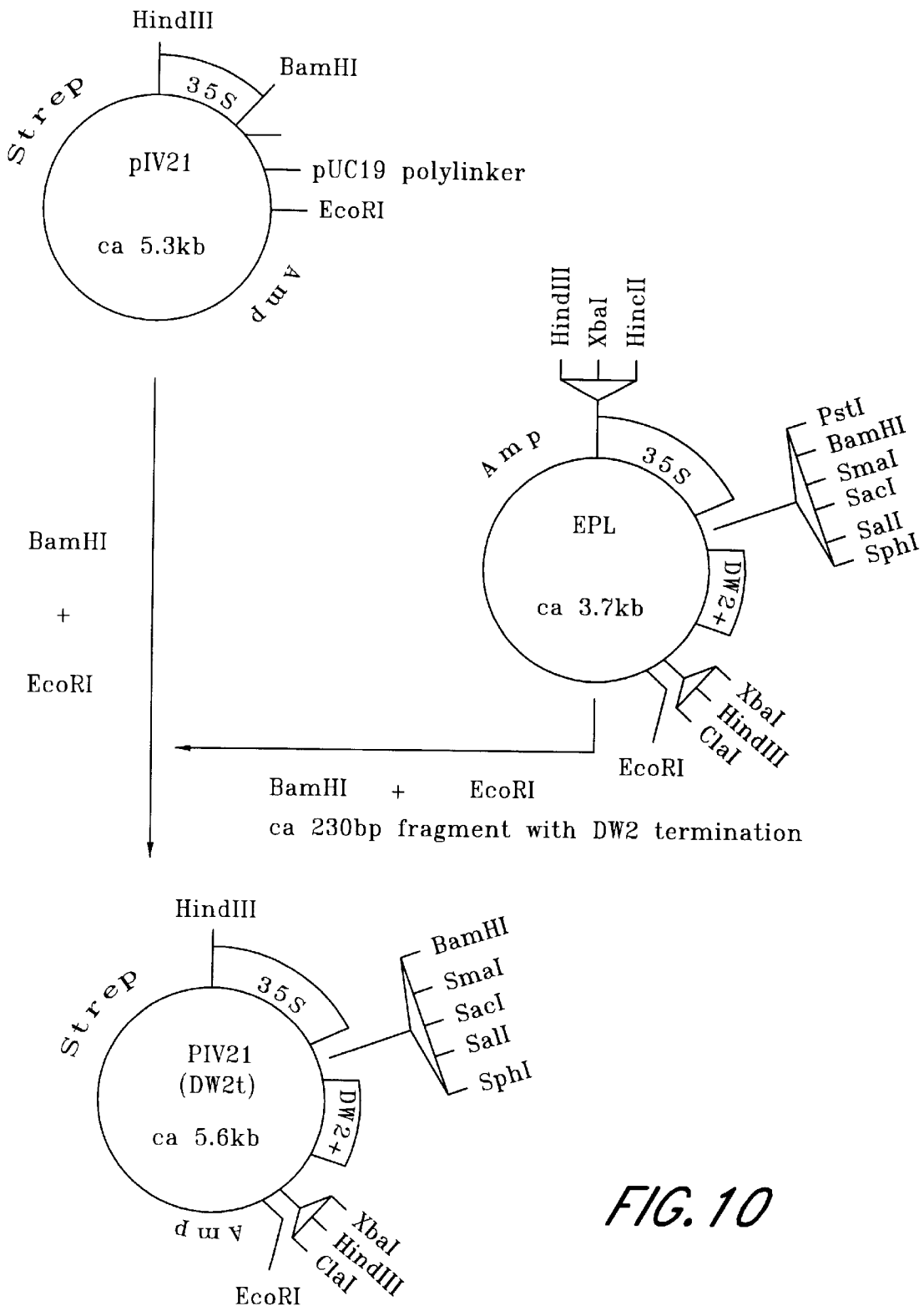
FIG. 10 is a map of pEPL.

The antisense α-amylase construction pJK4, containing the sequence shown as SEQ. I.D. No. 19, was made by using the SacI and EcoRV fragment from pAMYZ4 and subcloning it into an appropriate plasmid—such as SmaI and SacI digested pEPL plasmid (see FIG. 10). This places the antisense sequence downstream of an enhanced 35S promoter (E35S) and upstream of the DW2t terminator. This plasmid is called pEPLZ4Sac-Eco and a partial HindIII fragment containing the E35S promoter, the antisense potato sequence and the DW2t terminator was further subcloned into a HindIII digested pBI121, thereby creating the binary plasmid pJK4, see FIG. 9.

Other modifications of the present invention will be apparent to those skilled in the art without departing from the scope of the invention.

REFERENCES

1. Yanisch-Perron, C., Vieira, J., Messing, J. (1985) Gene 33:103–119
2. Brock, K., Beggs, J. D., Brammar, W. J., Hopkins, A. S. and Murray, N. E. (1976) Mol Gen Genet 146:199
3. Murray, N. E., Brammar, W. J. and Murray, K. (1977) Mol Gen Genet 150: 53
4. Hoekema et al (1983) Nature 303: 179–180
5. Frischauf A-M., Lehrach H., Poustka A., and Murray N. (1983) J Mol Biol 170, 827–842
6. Soberon, Covarrubias, Bolivar (1980) Gene 9, 287
7. Short, J. M., Fernandez, J. M., Sorge, J. A. and Huse, W. D. (1988) Nucleic Acids Res 16, 7583–7600
8. Bevan, M. W.(1984), Nucleic Acids Res 12, 8711–8721
9. Jefferson, R. A., Kavanagh, T. A. and Bevan, M. W. (1987) EMBO J 6, 3901–3907
10. Murashige, T. and Skoog, F. (1962) Physiol Plantarum 15: 473–497
11. Fischer, R. L. and Goldberg, R. B. (1982) Cell 29: 651
12. Stratagene cloning system, Custom library, 11099 North Torrey Pines Road La Jolla, Calif. 92037
13. Benton, W. D. and Davis, R. N. (1977) Science 196, 180–182
14. Sambrook, J., Fritsch, E. F. and Maniatis, T. (1989) Molecular cloning: A laboratory manual, 2nd ed. Cold Spring Harbor Laboratory Press
15. The Qiagenologist. Application Protocol. 2nd Edition. Qiagen.
16. Maniatis, T. et al. (1982) Molecular Cloning A Laboratory Manual. Cold Spring Harbour Laboratory Press
17. Southern, E. M. (1975) J Mol Biol 98: 503–517
18. Amersham Life Science protocol: Hybond™-N (N+; positively charged nylon membrane) Version 2.0.
19. Mandell, W and Higa, A. (1970), J Mol Biol 166, 557–580
20. Holters et al (1978) Mol Gen Genct 163: 181–187.
21. Linsmaier, E. U. and Skoog, F. (1965), Physiol. Plant. 18: 100–127
22. Chang H-H and Chang M-T (1991) Bot Bull Academia Sinica 32:63–70
23. Jefferson, R. A. (1987) Plant Mol Biol Rep 5: 387
24. Steege, G., Nieboer, M., Swaving, J. and Tempelaar, M. J. (1992) Plant Mol Biol 20: 19–30
25. Matton, D. P., Prescott, G., Bertrand, C., Camirand, A. and Brisson, N. (1993) Plant Mol Biol 22: 279–291
26. Ohta, S., Hattori, T., Morikami, A. and Nakamura, K. (1991) Mol Gen Genet 225: 369–378
27. Ueda, T., Pichersky, E., Malik, V. S. and Cashmore, A. R. (1989) Plant Cell 1:217–227
28. Stougaard, J., Sandahl, N. N., Grøn, A., Kühle, A. and Marcker, K. A. (1987) EMBO J 6: 3565–3569
29. Stougaard, J., Jørgensen, J. E., Christensen, T., Kühle, A. and Marcker, K. A. (1990) Mol Gen Genet 220, 353–360
30. Burow, M. D., Sen, P., Chlan, C. A. and Murai, N. (1992) Plant J 2: 537–548
31. Lorberth, R., Dammann, C., Ebneth, M., Armati, S. and Sanchez-Serrano, J. J. (1992) Plant J 2: 477–486
32. Bucher, P. and Trifonov, E. N. (1986) Nucl Acid Res 14, 10009–100026
33. Yamaguchi-Shinozaki, K. and Shinozaki, K. (1993) Mol Gen Genet 236: 331–340
34. Odell, J. T., Nagy, F. and Chua, N.-H. (1985) Nature 313:810
35. Abel, P. P. et al. (1986) Science 232: 738
36. Bevan, M. W., Mason , S. E. and Goclet, P. (1985) EMBO J 4:1921
37. Morelli, G., Nagy, F., Fraley, R. T., Rogers, S. G. and Chua, N.-H. (1985)
38. Shah, D. M. et al. (1978) Science 233:478

---

What is claimed is:

1. An isolated α-amylase promoter having cold-sensitive promoter activity, having a sequence comprising the 5.5 Kb EcoRI DNA fragment of *Solanum tuberosum* from the transformed *E. coli* strain, DH5alpha-gPAmy 351 (NCIMB Accession Number 40682).

2. The α-amylase promoter according to claim 1 operably linked to a gene of interest.

3. An expression vector comprising the α-amylase promoter according to claim 1.

4. A transformation vector comprising the α-amylase promoter according to claim 1.

5. A construct comprising the promoter as defined in claim 1 operably linked to a polynucleotide encoding an anti-sense α-amylase polynucleotide.

6. A transformed plant cell or transformed plant organ comprising the α-amylase promoter according to claim 1.

7. The transformed plant cell or transformed plant organ of claim 6, wherein said promoter is operably linked to a polynucleotide of interest.

8. A transgenic plant having a genome that comprises the α-amylase promoter according to claim 1 operably linked to a gene of interest.

9. The transgenic plant according to claim 8, wherein said transgenic plant is a potato plant.

10. A method of inducing expression of a polynucleotide of interest in plant cells, comprising the following steps:

a) making an expression construct that comprises the α-amylase promoter according to claim 1, operably linked to the polynucleotide of interest;

b) introducing said expression construct into cells of a plant to produce cells comprising the expression construct; and c) exposing said cells comprising the expression construct to a temperature in the range of from about 0° C. to about 12° C., thereby inducing expression of the polynucleotide of interest in the plant cells.

11. The method of claim 10, wherein said plant cells are in one or more plant tissues selected from the group consisting of: tuber, sprout, root, and stem.

12. An isolated α-amylase promoter having tuber-specific activity and having a sequence comprising SEQ ID NO: 1.

13. The α-amylase promoter according to claim 12 operably linked to a gene of interest.

14. An expression vector comprising the α-amylase promoter according to claim 12.

15. A transformation vector comprising the α-amylase promoter according to claim 12.

16. A transformed plant cell or transformed plant organ comprising the α-amylase promoter according to claim 12.

17. The transformed plant cell or transformed plant organ of claim 16, wherein said promoter is operably linked to a polynucleotide of interest.

18. A transgenic plant having a genome that comprises the α-amylase promoter according to claim 12 operably linked to a gene of interest.

19. A method of expressing a polynucleotide of interest in cells of a plant tuber, comprising the following steps:

a) making an expression construct that comprises the α-amylase promoter according to claim 12, operably linked to the polynucleotide of interest; and b) introducing said expression construct into cells of a plant tuber to produce cells comprising the expression construct, wherein the polynucleotide of interest is expressed in the cells of the plant tuber.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 166 base pairs
      (B) TYPE: nucleic acid
      (C) STRANDEDNESS: double
      (D) TOPOLOGY: linear (ii) MOLECULE TYPE: Genomic DNA (xi) SEQUENCE DESCRIPTION: SEQ ID NO: 1:

```
ATAGCTTGAG GCGAAAATAT TTAATAAAAA CACTTCTTAA TTTGTTTATA TGTTCAATTG      60

AACATGTCCG TGATTAGAAA ATTAAATTAA ATTCAATGAC AAATTTAATA ATTTGACACA     120

AAATTTATGA AAAAAATATC AAAATATAAA GAATATTTT TTTTGA                    166
```

(2) INFORMATION FOR SEQ ID NO: 2:

(i) SEQUENCE CHARACTERISTICS:
        (A) LENGTH: 291 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 2:

```
AAGCTTCCAA TGAACCGTTG CCATGTGTCA CTGCCTATTC ACCGCGAAAC ATGAATATCA    60
CTGACGAACG ATTTCGGAGC GGAACGAATC CAGAAAATGG ATTACTTTCT ATAAATTCCT   120
CGAATCTCAA CTCCATTTCG TAAAAATAAA ATTAAAAATA TTGTTTCTTT TTGTATTTCT   180
TTTTGTATTT CTGGTTTATG TGGTGATCGA ATTTTCAATT TTTTTACTGG TAGTGATTCC   240
TACTTTTCTT CAATTGCATT TCTCCTTTTT CCATTTCACG GTTGAGAATT C            291
```

(2) INFORMATION FOR SEQ ID NO: 3:

(i) SEQUENCE CHARACTERISTICS:
        (A) LENGTH: 508 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
AATGGATTAA AAAGAAAAAA AAAACAAATA AATTGAACCG GGATAAGTTG GTTGTTTAAT    60
TGATTATTGA TTATGATCTC AATTTGACAT TTTGCGCGAT CTTTCGACCT CAATTCGTAT   120
GAACTGACAC TACGCCAATG GACAGTCGCC GTCGTCACCG CCACCGCACT ATTCTCGACG   180
CGTCGTCTAT CTCCTCCACC CCACAGCCGT CAATTCCAAG CTTCCAATGA ACCGTTGCCA   240
TGTGTCACTG CCTATTCACC GCGAAACATG AATATCACTG ACGAACGATT TCGGAGCGGA   300
ACGAATCCAG AAAATGGATT ACTTTCTATA AATTCCTCGA ATCTCAACTC CATTTCGTAA   360
AAATAAAATT AAAAATATTG TTTCTTTTTG TATTTCTTTT TGTATTTCTG GTTTATGTGG   420
TGATCGAATT TTCAATTTTT TTACTGGTAG TGATTCCTAC TTTTCTTCAA TTGCATTTCT   480
CCTTTTTCCA TTTCACGGTT GAGAATTC                                     508
```

(2) INFORMATION FOR SEQ ID NO: 4:

(i) SEQUENCE CHARACTERISTICS:
        (A) LENGTH: 514 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

```
TTTTGAAATG GATTAAAAAG AAAAAAAAAA CAAATAAATT GAACCGGGAT AAGTTGGTTG    60
TTTAATTGAT TATTGATTAT GATCTCAATT TGACATTTTG CGCGATCTTT CGACCTCAAT   120
TCGTATGAAC TGACACTACG CCAATGGACA GTCGCCGTCG TCACCGCCAC CGCACTATTC   180
TCGACGCGTC GTCTATCTCC TCCACCCCAC AGCCGTCAAT TCCAAGCTTC CAATGAACCG   240
TTGCCATGTG TCACTGCCTA TTCACCGCGA AACATGAATA TCACTGACGA ACGATTTCGG   300
AGCGGAACGA ATCCAGAAAA TGGATTACTT TCTATAAATT CCTCGAATCT CAACTCCATT   360
TCGTAAAAAT AAAATTAAAA ATATTGTTTC TTTTTGTATT TCTTTTTGTA TTTCTGGTTT   420
```

```
ATGTGGTGAT CGAATTTTCA ATTTTTTTAC TGGTAGTGAT TCCTACTTTT CTTCAATTGC      480

ATTTCTCCTT TTTCCATTTC ACGGTTGAGA ATTC                                  514

(2) INFORMATION FOR SEQ ID NO: 5:

(i) SEQUENCE CHARACTERISTICS:
        (A) LENGTH: 518 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 5:

TTTTTTTTGA AATGGATTAA AAAGAAAAAA AAAACAAATA AATTGAACCG GGATAAGTTG       60

GTTGTTTAAT TGATTATTGA TTATGATCTC AATTTGACAT TTTGCGCGAT CTTTCGACCT      120

CAATTCGTAT GAACTGACAC TACGCCAATG GACAGTCGCC GTCGTCACCG CCACCGCACT      180

ATTCTCGACG CGTCGTCTAT CTCCTCCACC CCACAGCCGT CAATTCCAAG CTTCAATGA       240

ACCGTTGCCA TGTGTCACTG CCTATTCACC GCGAAACATG AATATCACTG ACGAACGATT      300

TCGGAGCGGA ACGAATCCAG AAAATGGATT ACTTTCTATA AATTCCTCGA ATCTCAACTC      360

CATTTCGTAA AATAAAATT AAAAATATTG TTTCTTTTTG TATTTCTTTT TGTATTTCTG       420

GTTTATGTGG TGATCGAATT TTCAATTTTT TTACTGGTAG TGATTCCTAC TTTTCTTCAA      480

TTGCATTTCT CCTTTTTCCA TTTCACGGTT GAGAATTC                              518

(2) INFORMATION FOR SEQ ID NO: 6:

(i) SEQUENCE CHARACTERISTICS:
        (A) LENGTH: 631 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 6:

GTTTATATGT TCAATTGAAC ATGTCCGTGA TTAGAAAATT AAATTAAATT CAATGACAAA       60

TTTAATAATT TGACACAAAA TTTATGAAAA AAATATCAAA ATATAAAGAA ATATTTTTTT      120

TGAAATGGAT TAAAAAGAAA AAAAAAACAA ATAAATTGAA CCGGGATAAG TTGGTTGTTT      180

AATTGATTAT TGATTATGAT CTCAATTTGA CATTTTGCGC GATCTTTCGA CCTCAATTCG      240

TATGAACTGA CACTACGCCA ATGGACAGTC GCCGTCGTCA CCGCCACCGC ACTATTCTCG      300

ACGCGTCGTC TATCTCCTCC ACCCCACAGC CGTCAATTCC AAGCTTCCAA TGAACCGTTG      360

CCATGTGTCA CTGCCTATTC ACCGCGAAAC ATGAATATCA CTGACGAACG ATTTCGGAGC      420

GGAACGAATC CAGAAAATGG ATTACTTTCT ATAAATTCCT CGAATCTCAA CTCCATTTCG      480

TAAAATAAA ATTAAAAATA TTGTTTCTTT TTGTATTTCT TTTTGTATTT CTGGTTTATG       540

TGGTGATCGA ATTTTCAATT TTTTACTGG TAGTGATTCC TACTTTTCTT CAATTGCATT       600

TCTCCTTTTT CCATTTCACG GTTGAGAATT C                                     631

(2) INFORMATION FOR SEQ ID NO: 7:

(i) SEQUENCE CHARACTERISTICS:
        (A) LENGTH: 674 base pairs
        (B) TYPE: nucleic acid
        (C) STRANDEDNESS: double
        (D) TOPOLOGY: linear
```

(ii) MOLECULE TYPE: DNA (genomic)

(xi) SEQUENCE DESCRIPTION: SEQ ID NO: 7:

| | | | | | |
|---|---|---|---|---|---|
| ATAGCTTGAG | GCGAAAATAT | TTAATAAAAA | CACTTCTTAA | TTTGTTTATA | TGTTCAATTG | 60 |
| AACATGTCCG | TGATTAGAAA | ATTAAATTAA | ATTCAATGAC | AAATTTAATA | ATTTGACACA | 120 |
| AAATTTATGA | AAAAAATATC | AAAATATAAA | GAAATATTTT | TTTTGAAATG | GATTAAAAAG | 180 |
| AAAAAAAAAA | CAAATAAATT | GAACCGGGAT | AAGTTGGTTG | TTTAATTGAT | TATTGATTAT | 240 |
| GATCTCAATT | TGACATTTTG | CGCGATCTTT | CGACCTCAAT | TCGTATGAAC | TGACACTACG | 300 |
| CCAATGGACA | GTCGCCGTCG | TCACCGCCAC | CGCACTATTC | TCGACGCGTC | GTCTATCTCC | 360 |
| TCCACCCCAC | AGCCGTCAAT | TCCAAGCTTC | CAATGAACCG | TTGCCATGTG | TCACTGCCTA | 420 |
| TTCACCGCGA | AACATGAATA | TCACTGACGA | ACGATTTCGG | AGCGGAACGA | ATCCAGAAAA | 480 |
| TGGATTACTT | TCTATAAATT | CCTCGAATCT | CAACTCCATT | TCGTAAAAAT | AAAATTAAAA | 540 |
| ATATTGTTTC | TTTTTGTATT | TCTTTTTGTA | TTTCTGGTTT | ATGTGGTGAT | CGAATTTTCA | 600 |
| ATTTTTTTAC | TGGTAGTGAT | TCCTACTTTT | CTTCAATTGC | ATTTCTCCTT | TTTCCATTTC | 660 |
| ACGGTTGAGA | ATTC | | | | | 674 |

(2) INFORMATION FOR SEQ ID NO: 8:

(i) SEQUENCE CHARACTERISTICS:
        (A) LENGTH: 687 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

| | | | | | |
|---|---|---|---|---|---|
| TTCCTTTCCT | CATATAGCTT | GAGGCGAAAA | TATTTAATAA | AAACACTTCT | TAATTTGTTT | 60 |
| ATATGTTCAA | TTGAACATGT | CCGTGATTAG | AAAATTAAAT | TAAATTCAAT | GACAAATTTA | 120 |
| ATAATTTGAC | ACAAAATTTA | TGAAAAAAAT | ATCAAAATAT | AAAGAAATAT | TTTTTTTGAA | 180 |
| ATGGATTAAA | AGAAAAAAAA | AAACAAATAA | ATTGAACCGG | GATAAGTTGG | TTGTTTAATT | 240 |
| GATTATTGAT | TATGATCTCA | ATTTGACATT | TTGCGCGATC | TTTCGACCTC | AATTCGTATG | 300 |
| AACTGACACT | ACGCCAATGG | ACAGTCGCCG | TCGTCACCGC | CACCGCACTA | TTCTCGACGC | 360 |
| GTCGTCTATC | TCCTCCACCC | CACAGCCGTC | AATTCCAAGC | TTCCAATGAA | CCGTTGCCAT | 420 |
| GTGTCACTGC | CTATTCACCG | CGAAACATGA | ATATCACTGA | CGAACGATTT | CGGAGCGGAA | 480 |
| CGAATCCAGA | AAATGGATTA | CTTTCTATAA | ATTCCTCGAA | TCTCAACTCC | ATTTCGTAAA | 540 |
| AATAAAATTA | AAAATATTGT | TTCTTTTTGT | ATTTCTTTTT | GTATTTCTGG | TTTATGTGGT | 600 |
| GATCGAATTT | TCAATTTTTT | TACTGGTAGT | GATTCCTACT | TTTCTTCAAT | TGCATTTCTC | 660 |
| CTTTTTCCAT | TTCACGGTTG | AGAATTC | | | | 687 |

(2) INFORMATION FOR SEQ ID NO: 9:

(i) SEQUENCE CHARACTERISTICS:
        (A) LENGTH: 693 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 9:

```
CACTGATTCC TTTCCTCATA TAGCTTGAGG CGAAAATATT TAATAAAAAC ACTTCTTAAT    60

TTGTTTATAT GTTCAATTGA ACATGTCCGT GATTAGAAAA TTAAATTAAA TTCAATGACA   120

AATTTAATAA TTTGACACAA AATTTATGAA AAAAATATCA AAATATAAAG AAATATTTTT   180

TTTGAAATGG ATTAAAAAGA AAAAAAAAAC AAATAAATTG AACCGGGATA AGTTGGTTGT   240

TTAATTGATT ATTGATTATG ATCTCAATTT GACATTTTGC GCGATCTTTC GACCTCAATT   300

CGTATGAACT GACACTACGC AATGGACAG TCGCCGTCGT CACCGCCACC GCACTATTCT    360

CGACGCGTCG TCTATCTCCT CCACCCCACA GCCGTCAATT CCAAGCTTCC AATGAACCGT   420

TGCCATGTGT CACTGCCTAT TCACCGCGAA ACATGAATAT CACTGACGAA CGATTTCGGA   480

GCGGAACGAA TCCAGAAAAT GGATTACTTT CTATAAATTC CTCGAATCTC AACTCCATTT   540

CGTAAAAATA AAATTAAAAA TATTGTTTCT TTTTGTATTT CTTTTTGTAT TTCTGGTTTA   600

TGTGGTGATC GAATTTTCAA TTTTTTTACT GGTAGTGATT CCTACTTTTC TTCAATTGCA   660

TTTCTCCTTT TTCCATTTCA CGGTTGAGAA TTC                                693

(2) INFORMATION FOR SEQ ID NO: 10:

(i) SEQUENCE CHARACTERISTICS:
        (A) LENGTH: 758 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 10:

CTTGCGCCTT TCCCTAAATT AAGTAAAACT CTTCGCCTCA TGCCTTACGC CTCCGCCTTT    60

TAAAACACTG ATTCCTTTCC TCATATAGCT TGAGGCGAAA ATATTTAATA AAAACACTTC   120

TTAATTTGTT TATATGTTCA ATTGAACATG TCCGTGATTA GAAAATTAAA TTAAATTCAA   180

TGACAAATTT AATAATTTGA CACAAAATTT ATGAAAAAAA TATCAAAATA TAAAGAAATA   240

TTTTTTTTGA AATGGATTAA AAAGAAAAAA AAACAAATAA AATTGAACCG GATAAGTTG    300

GTTGTTTAAT TGATTATTGA TTATGATCTC AATTTGACAT TTTGCGCGAT CTTTCGACCT   360

CAATTCGTAT GAACTGACAC TACGCCAATG GACAGTCGCC GTCGTCACCG CCACCGCACT   420

ATTCTCGACG CGTCGTCTAT CTCCTCCACC CCACAGCCGT CAATTCCAAG CTTCCAATGA   480

ACCGTTGCCA TGTGTCACTG CCTATTCACC GCGAAACATG AATATCACTG ACGAACGATT   540

TCGGAGCGGA ACGAATCCAG AAAATGGATT ACTTTCTATA AATTCCTCGA ATCTCAACTC   600

CATTTCGTAA AATAAAATT AAAAATATTG TTTCTTTTTG TATTTCTTTT TGTATTTCTG    660

GTTTATGTGG TGATCGAATT TTCAATTTTT TTACTGGTAG TGATTCCTAC TTTTCTTCAA   720

TTGCATTTCT CCTTTTTCCA TTTCACGGTT GAGAATTC                            758

(2) INFORMATION FOR SEQ ID NO: 11:

(i) SEQUENCE CHARACTERISTICS:
        (A) LENGTH: 855 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 11:

CAAATTTTGA TGTATTTTTA TAATTTTGTA TTATTATATT ATTATACTAT ATTTAAAAAT    60

TTAAAGATCC ATAGGGCTTA CGCCCCACGT CAAGAGGCTT GCGCCTTTCC CTAAATTAAG   120
```

```
TAAAACTCTT CGCCTCATGC CTTACGCCTC CGCCTTTTAA AACACTGATT CCTTTCCTCA        180

TATAGCTTGA GGCGAAAATA TTTAATAAAA ACACTTCTTA ATTTGTTTAT ATGTTCAATT        240

GAACATGTCC GTGATTAGAA AATTAAATTA AATTCAATGA CAAATTTAAT AATTTGACAC        300

AAAATTTATG AAAAAAATAT CAAAATATAA AGAAATATTT TTTTTGAAAT GGATTAAAAA        360

GAAAAAAAAA ACAAATAAAT TGAACCGGGA TAAGTTGGTT GTTTAATTGA TTATTGATTA        420

TGATCTCAAT TTGACATTTT GCGCGATCTT TCGACCTCAA TTCGTATGAA CTGACACTAC        480

GCCAATGGAC AGTCGCCGTC GTCACCGCCA CCGCACTATT CTCGACGCGT CGTCTATCTC        540

CTCCACCCCA CAGCCGTCAA TTCCAAGCTT CCAATGAACC GTTGCCATGT GTCACTGCCT        600

ATTCACCGCG AAACATGAAT ATCACTGACG AACGATTTCG GAGCGGAACG AATCCAGAAA        660

ATGGATTACT TTCTATAAAT TCCTCGAATC TCAACTCCAT TTCGTAAAAA TAAAATTAAA        720

AATATTGTTT CTTTTTGTAT TTCTTTTTGT ATTTCTGGTT TATGTGGTGA TCGAATTTTC        780

AATTTTTTTA CTGGTAGTGA TTCCTACTTT TCTTCAATTG CATTTCTCCT TTTTCCATTT        840

CACGGTTGAG AATTC                                                        855

(2) INFORMATION FOR SEQ ID NO: 12:

(i) SEQUENCE CHARACTERISTICS:
        (A) LENGTH: 859 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 12:

ATTTCAAATT TTGATGTATT TTTATAATTT TGTATTATTA TATTATTATA CTATATTTAA         60

AAATTTAAAG ATCCATAGGG CTTACGCCCC ACGTCAAGAG GCTTGCGCCT TTCCCTAAAT        120

TAAGTAAAAC TCTTCGCCTC ATGCCTTACG CCTCCGCCTT TTAAAACACT GATTCCTTTC        180

CTCATATAGC TTGAGGCGAA ATATTTAAT AAAAACACTT CTTAATTTGT TTATATGTTC         240

AATTGAACAT GTCCGTGATT AGAAAATTAA ATTAAATTCA ATGACAAATT TAATAATTTG       300

ACACAAAATT TATGAAAAAA ATATCAAAAT ATAAAGAAAT ATTTTTTTTG AAATGGATTA       360

AAAAGAAAAA AAAAACAAAT AAATTGAACC GGGATAAGTT GGTTGTTTAA TTGATTATTG       420

ATTATGATCT CAATTTGACA TTTTGCGCGA TCTTTCGACC TCAATTCGTA TGAACTGACA       480

CTACGCCAAT GGACAGTCGC CGTCGTCACC GCCACCGCAC TATTCTCGAC GCGTCGTCTA       540

TCTCCTCCAC CCCACAGCCG TCAATTCCAA GCTTCCAATG AACCGTTGCC ATGTGTCACT       600

GCCTATTCAC CGCGAAACAT GAATATCACT GACGAACGAT TTCGGAGCGG AACGAATCCA       660

GAAAATGGAT TACTTTCTAT AAATTCCTCG AATCTCAACT CCATTTCGTA AAAATAAAAT       720

TAAAATATT GTTTCTTTTT GTATTTCTTT TTGTATTTCT GGTTTATGTG GTGATCGAAT        780

TTTCAATTTT TTTACTGGTA GTGATTCCTA CTTTTCTTCA ATTGCATTTC TCCTTTTTCC       840

ATTTCACGGT TGAGAATTC                                                   859

(2) INFORMATION FOR SEQ ID NO: 13:

(i) SEQUENCE CHARACTERISTICS:
        (A) LENGTH: 1214 base pairs
        (B) TYPE: nucleic acid
        (C) STRANDEDNESS: double
        (D) TOPOLOGY: linear
```

(ii) MOLECULE TYPE: DNA (genomic)

(xi) SEQUENCE DESCRIPTION: SEQ ID NO: 13:

| | | | | | |
|---|---|---|---|---|---|
| GAAGGTGATT | ATACATTACG | TAACATTTCT | TTTAAAAATA | TGTAAGCAAA | TTTACTTTTT | 60 |
| AACTTATCAT | TGATCTTCAT | GGTTTTGTCA | TAAATCTCAA | AGTTATCATA | TTTTATATAG | 120 |
| CTATTTGAAA | GTAATTTTAT | TTTTACTCAT | CATTGAGTGA | TGCTTTTATT | ATAATACTAG | 180 |
| TAAGTTTTAT | TTATTATTTT | CTTTTAGGGG | TGAATTGTAT | AATATAATAA | AAAATATATT | 240 |
| TTTAGAAATA | ATGATTCTTT | TATTATTAAA | AAGTTAAGAT | ATTAGATTAT | TTATGCTTGT | 300 |
| ATAATAATGA | ACGAAGTTTT | ATTTTCTATG | AGTTTCATTA | ATCATGTTTG | TAATTATTTC | 360 |
| AAATTTTGAT | GTATTTTTAT | AATTTTGTAT | TATTATATTA | TTATACTATA | TTTAAAAATT | 420 |
| TAAAGATCCA | TAGGGCTTAC | GCCCCACGTC | AAGAGGCTTG | CGCCTTTCCC | TAAATTAAGT | 480 |
| AAAACTCTTC | GCCTCATGCC | TTACGCCTCC | GCCTTTTAAA | ACACTGATTC | CTTTCCTCAT | 540 |
| ATAGCTTGAG | GCGAAAATAT | TTAATAAAAA | CACTTCTTAA | TTTGTTTATA | TGTTCAATTG | 600 |
| AACATGTCCG | TGATTAGAAA | ATTAAATTAA | ATTCAATGAC | AAATTTAATA | ATTTGACACA | 660 |
| AAATTTATGA | AAAAAATATC | AAAATATAAA | GAAATATTTT | TTTTGAAATG | GATTAAAAAG | 720 |
| AAAAAAAAAA | CAAATAAATT | GAACCGGGAT | AAGTTGGTTG | TTTAATTGAT | TATTGATTAT | 780 |
| GATCTCAATT | TGACATTTTG | CGCGATCTTT | CGACCTCAAT | TCGTATGAAC | TGACACTACG | 840 |
| CCAATGGACA | GTCGCCGTCG | TCACCGCCAC | CGCACTATTC | TCGACGCGTC | GTCTATCTCC | 900 |
| TCCACCCCAC | AGCCGTCAAT | TCCAAGCTTC | CAATGAACCG | TTGCCATGTG | TCACTGCCTA | 960 |
| TTCACCGCGA | AACATGAATA | TCACTGACGA | ACGATTTCGG | AGCGGAACGA | ATCCAGAAAA | 1020 |
| TGGATTACTT | TCTATAAATT | CCTCGAATCT | CAACTCCATT | TCGTAAAAAT | AAAATTAAAA | 1080 |
| ATATTGTTTC | TTTTTGTATT | TCTTTTTGTA | TTTCTGGTTT | ATGTGGTGAT | CGAATTTTCA | 1140 |
| ATTTTTTTAC | TGGTAGTGAT | TCCTACTTTT | CTTCAATTGC | ATTTCTCCTT | TTTCCATTTC | 1200 |
| ACGGTTGAGA | ATTC | | | | | 1214 |

(2) INFORMATION FOR SEQ ID NO: 14:

(i) SEQUENCE CHARACTERISTICS:
        (A) LENGTH: 1232 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 14:

| | | | | | |
|---|---|---|---|---|---|
| ACTATTTGAT | AACATTATGA | AGGTGATTAT | ACATTACGTA | ACATTTCTTT | TAAAAATATG | 60 |
| TAAGCAAATT | TACTTTTTAA | CTTATCATTG | ATCTTCATGG | TTTTGTCATA | AATCTCAAAG | 120 |
| TTATCATATT | TTATATAGCT | ATTTGAAAGT | AATTTTATTT | TTACTCATCA | TTGAGTGATG | 180 |
| CTTTTATTAT | AATACTAGTA | AGTTTTATTT | ATTATTTTCT | TTTAGGGGTG | AATTGTATAA | 240 |
| TATAATAAAA | AATATATTTT | TAGAAATAAT | GATTCTTTTA | TTATTAAAAA | GTTAAGATAT | 300 |
| TAGATTATTT | ATGCTTGTAT | AATAATGAAC | GAAGTTTTAT | TTTCTATGAG | TTTCATTAAT | 360 |
| CATGTTTGTA | ATTATTTCAA | ATTTTGATGT | ATTTTTATAA | TTTTGTATTA | TTATATTATT | 420 |
| ATACTATATT | TAAAAATTTA | AAGATCCATA | GGGCTTACGC | CCCACGTCAA | GAGGCTTGCG | 480 |
| CCTTTCCCTA | AATTAAGTAA | AACTCTTCGC | CTCATGCCTT | ACGCCTCCGC | CTTTTAAAAC | 540 |
| ACTGATTCCT | TTCCTCATAT | AGCTTGAGGC | GAAAATATTT | AATAAAAACA | CTTCTTAATT | 600 |

-continued

| | |
|---|---|
| TGTTTATATG TTCAATTGAA CATGTCCGTG ATTAGAAAAT TAAATTAAAT TCAATGACAA | 660 |
| ATTTAATAAT TTGACACAAA ATTTATGAAA AAAATATCAA AATATAAAGA AATATTTTTT | 720 |
| TTGAAATGGA TTAAAAAGAA AAAAAAAACA AATAAATTGA ACCGGGATAA GTTGGTTGTT | 780 |
| TAATTGATTA TTGATTATGA TCTCAATTTG ACATTTTGCG CGATCTTTCG ACCTCAATTC | 840 |
| GTATGAACTG ACACTACGCC AATGGACAGT CGCCGTCGTC ACCGCCACCG CACTATTCTC | 900 |
| GACGCGTCGT CTATCTCCTC CACCCCACAG CCGTCAATTC CAAGCTTCCA ATGAACCGTT | 960 |
| GCCATGTGTC ACTGCCTATT CACCGCGAAA CATGAATATC ACTGACGAAC GATTTCGGAG | 1020 |
| CGGAACGAAT CCAGAAAATG GATTACTTTC TATAAATTCC TCGAATCTCA ACTCCATTTC | 1080 |
| GTAAAAATAA AATTAAAAAT ATTGTTTCTT TTTGTATTTC TTTTTGTATT TCTGGTTTAT | 1140 |
| GTGGTGATCG AATTTTCAAT TTTTTTACTG GTAGTGATTC CTACTTTTCT TCAATTGCAT | 1200 |
| TTCTCCTTTT TCCATTTCAC GGTTGAGAAT TC | 1232 |

(2) INFORMATION FOR SEQ ID NO: 15:

(i) SEQUENCE CHARACTERISTICS:
        (A) LENGTH: 1352 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 15:

| | |
|---|---|
| GGCCTCACAT CAACCTTCAT AATTCTTGAA TGAATGAATG ATAGACTTCA TAATTTTTTA | 60 |
| ACCTATACAT ATAAGAAAAT TGAGAGTAAC TCAAATAACA AGTTGTAGTA TCACATCTTT | 120 |
| ACTATTTGAT AACATTATGA AGGTGATTAT ACATTACGTA ACATTTCTTT TAAAAATATG | 180 |
| TAAGCAAATT TACTTTTTAA CTTATCATTG ATCTTCATGG TTTTGTCATA AATCTCAAAG | 240 |
| TTATCATATT TTATATAGCT ATTTGAAAGT AATTTTATTT TTACTCATCA TTGAGTGATG | 300 |
| CTTTTATTAT AATACTAGTA AGTTTTATTT ATTATTTTCT TTTAGGGGTG AATTGTATAA | 360 |
| TATAATAAAA AATATATTTT TAGAAATAAT GATTCTTTTA TTATTAAAAA GTTAAGATAT | 420 |
| TAGATTATTT ATGCTTGTAT AATAATGAAC GAAGTTTTAT TTTCTATGAG TTTCATTAAT | 480 |
| CATGTTTGTA ATTATTTCAA ATTTTGATGT ATTTTTATAA TTTTGTATTA TTATATTATT | 540 |
| ATACTATATT TAAAAATTTA AAGATCCATA GGGCTTACGC CCCACGTCAA GAGGCTTGCG | 600 |
| CCTTTCCCTA AATTAAGTAA AACTCTTCGC CTCATGCCTT ACGCCTCCGC CTTTTAAAAC | 660 |
| ACTGATTCCT TTCCTCATAT AGCTTGAGGC GAAAATATTT AATAAAAACA CTTCTTAATT | 720 |
| TGTTTATATG TTCAATTGAA CATGTCCGTG ATTAGAAAAT TAAATTAAAT TCAATGACAA | 780 |
| ATTTAATAAT TTGACACAAA ATTTATGAAA AAAATATCAA AATATAAAGA AATATTTTTT | 840 |
| TTGAAATGGA TTAAAAAGAA AAAAAAAACA AATAAATTGA ACCGGGATAA GTTGGTTGTT | 900 |
| TAATTGATTA TTGATTATGA TCTCAATTTG ACATTTTGCG CGATCTTTCG ACCTCAATTC | 960 |
| GTATGAACTG ACACTACGCC AATGGACAGT CGCCGTCGTC ACCGCCACCG CACTATTCTC | 1020 |
| GACGCGTCGT CTATCTCCTC CACCCCACAG CCGTCAATTC CAAGCTTCCA ATGAACCGTT | 1080 |
| GCCATGTGTC ACTGCCTATT CACCGCGAAA CATGAATATC ACTGACGAAC GATTTCGGAG | 1140 |
| CGGAACGAAT CCAGAAAATG GATTACTTTC TATAAATTCC TCGAATCTCA ACTCCATTTC | 1200 |
| GTAAAAATAA AATTAAAAAT ATTGTTTCTT TTTGTATTTC TTTTTGTATT TCTGGTTTAT | 1260 |
| GTGGTGATCG AATTTTCAAT TTTTTTACTG GTAGTGATTC CTACTTTTCT TCAATTGCAT | 1320 |

(2) INFORMATION FOR SEQ ID NO: 16:

(i) SEQUENCE CHARACTERISTICS:
        (A) LENGTH: 1734 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 16:

```
TCTTTAAGTT GTTTGCTTGA TTTTTCTTCT TCAATCTTCT ATATTTAATT CGTTTTAGCT    60
TCAAACTTCT TCAATTTTAT TTCAATTTAA TTCTACAAAA AAAATCTCTA TTTAGCACCA   120
TTCATAAAAT TCATGCTCAA AATGGGCAAA CATAAATAAT AAATGTGAAG TAAATAATGG   180
ATTAAAATAT ATATTTTTGG GCCTCACATC AACCTTCATA ATTCTTGAAT GAATGAATGA   240
TAGACTTCAT AATTTTTTAA CCTATACATA TAAGAAAATT GAGAGTAACT CAAATAACAA   300
GTTGTAGTAT CACATCTTTA CTATTTGATA ACATTATGAA GGTGATTATA CATTACGTAA   360
CATTTCTTTT AAAAATATGT AAGCAAATTT ACTTTTTAAC TTATCATTGA TCTTCATGGT   420
TTTGTCATAA ATCTCAAAGT TATCATATTT TATATAGCTA TTTGAAAGTA ATTTTATTTT   480
TACTCATCAT TGAGTGATGC TTTTATTATA ATACTAGTAA GTTTTATTTA TTATTTTCTT   540
TTAGGGGTGA ATTGTATAAT ATAATAAAAA ATATATTTTT AGAAATAATG ATTCTTTTAT   600
TATTAAAAAG TTAAGATATT AGATTATTTA TGCTTGTATA ATAATGAACG AAGTTTTATT   660
TTCTATGAGT TTCATTAATC ATGTTTGTAA TTATTTCAAA TTTTGATGTA TTTTTATAAT   720
TTTGTATTAT TATATTATTA TACTATATTT AAAAATTTAA AGATCCATAG GGCTTACGCC   780
CCACGTCAAG AGGCTTGCGC CTTTCCCTAA ATTAAGTAAA ACTCTTCGCC TCATGCCTTA   840
CGCCTCCGCC TTTTAAAACA CTGATTCCTT TCCTCATATA GCTTGAGGCG AAAATATTTA   900
ATAAAAACAC TTCTTAATTT GTTTATATGT TCAATTGAAC ATGTCCGTGA TTAGAAAATT   960
AAATTAAATT CAATGACAAA TTTAATAATT TGACACAAAA TTTATGAAAA AAATATCAAA  1020
ATATAAAGAA ATATTTTTTT TGAAATGGAT TAAAAGAAA AAAAAAACAA ATAAATTGAA  1080
CCGGGATAAG TTGGTTGTTT AATTGATTAT TGATTATGAT CTCAATTTGA CATTTTGCGC  1140
GATCTTTCGA CCTCAATTCG TATGAACTGA CACTACGCCA ATGGACAGTC GCCGTCGTCA  1200
CCGCCACCGC ACTATTCTCG ACGCGTCGTC TATCTCCTCC ACCCCACAGC CGTCAATTCC  1260
AAGCTTCCAA TGAACCGTTG CCATGTGTCA CTGCCTATTC ACCGCGAAAC ATGAATATCA  1320
CTGACGAACG ATTTCGGAGC GGAACGAATC CAGAAAATGG ATTACTTTCT ATAAATTCCT  1380
CGAATCTCAA CTCCATTTCG TAAAAATAAA ATTAAAAATA TTGTTTCTTT TTGTATTTCT  1440
TTTTGTATTT CTGGTTTATG TGGTGATCGA ATTTTCAATT TTTTTACTGG TAGTGATTCC  1500
TACTTTTCTT CAATTGCATT TCTCCTTTTT CCATTTCACG GTTGAGAATT CATGATTCCT  1560
TATCAGAGGA ATCGATCCGA TTTGACTAAT TTCACTTTTC GTCTGTATAA ATACCAGAGT  1620
ATCTAGGTTG AGGAACGTAA TTTCAAGCTG CGATCGGCTT TTTCCCCTGA ACGAGCAAAC  1680
ACAGGTTGTG GGTTCGAGTT AGCAAGGGAC GTATAATCTC AACTACAATC CATT         1734
```

(2) INFORMATION FOR SEQ ID NO: 17:

(i) SEQUENCE CHARACTERISTICS:
        (A) LENGTH: 1920 base pairs
        (B) TYPE: nucleic acid

TTCTCCTTTT TCCATTTCAC GGTTGAGAAT TC    1352

```
        (C) STRANDEDNESS: double
        (D) TOPOLOGY: linear (ii) MOLECULE TYPE: DNA (genomic)

(xi) SEQUENCE DESCRIPTION: SEQ ID NO: 17:

TCTTTAAGTT GTTTGCTTGA TTTTTCTTCT TCAATCTTCT ATATTTAATT CGTTTTAGCT      60

TCAAACTTCT TCAATTTTAT TTCAATTTAA TTCTACAAAA AAAATCTCTA TTTAGCACCA     120

TTCATAAAAT TCATGCTCAA AATGGGCAAA CATAAATAAT AAATGTGAAG TAAATAATGG     180

ATTAAAATAT ATATTTTTGG GCCTCACATC AACCTTCATA ATTCTTGAAT GAATGAATGA     240

TAGACTTCAT AATTTTTTAA CCTATACATA TAAGAAAATT GAGAGTAACT CAAATAACAA     300

GTTGTAGTAT CACATCTTTA CTATTTGATA ACATTATGAA GGTGATTATA CATTACGTAA     360

CATTTCTTTT AAAAATATGT AAGCAAATTT ACTTTTTAAC TTATCATTGA TCTTCATGGT     420

TTTGTCATAA ATCTCAAAGT TATCATATTT TATATAGCTA TTTGAAAGTA ATTTTATTTT     480

TACTCATCAT TGAGTGATGC TTTTATTATA ATACTAGTAA GTTTTATTTA TTATTTTCTT     540

TTAGGGGTGA ATTGTATAAT ATAATAAAAA ATATATTTTT AGAAATAATG ATTCTTTTAT     600

TATTAAAAAG TTAAGATATT AGATTATTTA TGCTTGTATA ATAATGAACG AAGTTTTATT     660

TTCTATGAGT TTCATTAATC ATGTTTGTAA TTATTTCAAA TTTTGATGTA TTTTTATAAT     720

TTTGTATTAT TATATTATTA TACTATATTT AAAAATTTAA AGATCCATAG GGCTTACGCC     780

CCACGTCAAG AGGCTTGCGC CTTTCCCTAA ATTAAGTAAA ACTCTTCGCC TCATGCCTTA     840

CGCCTCCGCC TTTTAAAACA CTGATTCCTT TCCTCATATA GCTTGAGGCG AAAATATTTA     900

ATAAAAACAC TTCTTAATTT GTTTATATGT TCAATTGAAC ATGTCCGTGA TTAGAAAATT     960

AAATTAAATT CAATGACAAA TTTAATAATT TGACACAAAA TTTATGAAAA AAATATCAAA    1020

ATATAAAGAA ATATTTTTTT TGAAATGGAT TAAAAGAAA AAAAAAACAA ATAAATTGAA    1080

CCGGGATAAG TTGGTTGTTT AATTGATTAT TGATTATGAT CTCAATTTGA CATTTTGCGC    1140

GATCTTTCGA CCTCAATTCG TATGAACTGA CACTACGCCA ATGGACAGTC GCCGTCGTCA    1200

CCGCCACCGC ACTATTCTCG ACGCGTCGTC TATCTCCTCC ACCCCACAGC CGTCAATTCC    1260

AAGCTTCCAA TGAACCGTTG CCATGTGTCA CTGCCTATTC ACCGCGAAAC ATGAATATCA    1320

CTGACGAACG ATTTCGGAGC GGAACGAATC CAGAAAATGG ATTACTTTCT ATAAATTCCT    1380

CGAATCTCAA CTCCATTTCG TAAAAATAAA ATTAAAAATA TTGTTTCTTT TTGTATTTCT    1440

TTTTGTATTT CTGGTTTATG TGGTGATCGA ATTTTCAATT TTTTTACTGG TAGTGATTCC    1500

TACTTTTCTT CAATTGCATT TCTCCTTTTT CCATTTCACG GTTGAGAATT CATGATTCCT    1560

TATCAGAGGA ATCGATCCGA TTTGACTAAT TTCACTTTTC GTCTGTATAA ATACCAGAGT    1620

ATCTAGGTTG AGGAACGTAA TTTCAAGCTG CGATCGGCTT TTTCCCCTGA ACGAGCAAAC    1680

ACAGGTTGTG GGTTCGAGTT AGCAAGGGAC GTATAATCTC AACTACAATC CATTATGGCG    1740

CTTGATGAAA GTCAGCAGTC TGATCCATGT AAGGTTCTCT TTTCCTTTAT ATATGCTTCA    1800

TAATTGAGAA GGAAGACGGA GATTTGAACT TAATAAAGGC GAAGATTTGA ACAAAATATT    1860

TTGGTATTTC ATTTAAAACT TTACCAGTTC TAAGAGTAAA TGATTGGGAT GTGCATGTCC    1920

(2) INFORMATION FOR SEQ ID NO: 18:

(i) SEQUENCE CHARACTERISTICS:
        (A) LENGTH: 1570 base pairs
        (B) TYPE: nucleic acid
        (C) STRANDEDNESS: double
        (D) TOPOLOGY: linear
```

(ii) MOLECULE TYPE: DNA (genomic)

(xi) SEQUENCE DESCRIPTION: SEQ ID NO: 18:

```
TGTGGTGATC GAATTTTCAA TTTTTTTACT GAGTATCTAG GTTGAGGAAC GTAATTTCAA      60

GCTGCGATCG GCTTTTTCCC CTGAACGAGC AAACACAGGT TGTGGGTTCG AGTTAGCAAG     120

GGACGTATAA TCTCAACTAC AATCCATTAT GGCGCTTGAT GAAAGTCAGC AGTCTGATCC     180

ATTGGTTGTG ATACGCAATG GAAAGGAGAT CATATTGCAG GCATTCGACT GGAATCTCA      240

TAAACATGAT TGGTGGCTAA ATTTAGATAC GAAAGTTCCT GATATTGCAA AGTCTGGTTT     300

CACAACTGCT TGGCTGCCTC CGGTGTGTCA GTCATTGGCT CCTGAAGGTT ACCTTCCACA     360

GAACCTTTAT TCTCTCAATT CTAAATATGG TTCTGAGGAT CTCTTAAAAG CTTTACTTAA     420

TAAGATGAAG CAGTACAAAG TTAGAGCGAT GGCGGACATA GTCATTAACC ACCGTGTTGG     480

GACTACTCAA GGGCATGGTG GAATGTACAA CCGCTATGAT GGAATTCCTA TGTCTTGGGA     540

TGAACATGCT ATTACATCTT GCACTGGTGG AAGGGGTAAC AAAAGCACTG GAGACAACTT     600

TAATGGAGTT CCAAATATAG ATCATACACA ATCCTTTGTT CGGAAAGATC TCATTGACTG     660

GATGCGGTGG CTAAGATCCT CTGTTGGCTT CCAAGATTTT CGTTTTGATT TTGCCAAAGG     720

TTATGCTTCA AAGTATGTAA AGGAATATAT CGAGGGAGCT GAGCCAATAT TTGCAGTTGG     780

AGAATACTGG GACACTTGCA ATTACAAGGG CAGCAATTTG GATTACAACC AAGATAGTCA     840

CAGGCAAAGA ATCATCAATT GGATTGATGG CGCGGGACAA CTTTCAACTG CATTCGATTT     900

TACAACAAAA GCAGTCCTTC AGGAAGCAGT CAAAGGAGAA TTCTGGCGTT TGCGTGACTC     960

TAAGGGGAAG CCCCCAGGAG TTTTAGGATT GTGGCCTTCA AGGGCTGTCA CTTTTATTGA    1020

TAATCACGAC ACTGGATCAA CTCAGGCGCA TTGGCCTTTC CCTTCACGTC ATGTTATGGA    1080

GGGCTATGCA TACATTCTTA CACACCCAGG GATACCATCA GTTTTCTTTG ACCATTTCTA    1140

CGAATGGGAT AATTCCATGC ATGACCAAAT TGTAAAGCTG ATTGCTATTC GGAGGAATCA    1200

AGGCATACAC AGCCGTTCAT CTATAAGAAT TCTTGAGGCA CAGCCAAACT TATACGCTGC    1260

AACCATTGAT GAAAAGGTTA GCGTGAAGAT TGGGGACGGA TCATGGAGCC CTGCTGGGAA    1320

AGAGTGGACT CTCGCGACCA GTGGCCATCG CTATGCAGTC TGGCAGAAGT AATCTTACAG    1380

CTATTCCGTT ACTTAATATA TTAGTAGAAA TATATATGTT TTAAACCCGA GCACCTACTT    1440

CTAACACTAG ATCCGCCTCT ACAGGCTTGG ATGGAGTGAT GAGTTTTTTT TTCCTGTTCA    1500

TTAGACATTG CAACATGGGA TGTATGTTTT GTTAATAAAA GTGTTCTTGA TCAATGCAAT    1560

GTAATAAGGG                                                          1570
```

(2) INFORMATION FOR SEQ ID NO: 19:

(i) SEQUENCE CHARACTERISTICS:
            (A) LENGTH: 1570 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 19:

```
ACACCACTAG CTTAAAAGTT AAAAAAATGA CTCATAGATC CAACTCCTTG CATTAAAGTT      60

CGACGCTAGC CGAAAAAGGG GACTTGCTCG TTTGTGTCCA ACACCCAAGC TCAATCGTTC     120

CCTGCATATT AGAGTTGATG TTAGGTAATA CCGCGAACTA CTTTCAGTCG TCAGACTAGG     180

TAACCAACAC TATGCGTTAC CTTTCCTCTA GTATAACGTC CGTAAGCTGA CCCTTAGAGT     240
```

```
ATTTGTACTA ACCACCGATT TAAATCTATG CTTTCAAGGA CTATAACGTT TCAGACCAAA      300

GTGTTGACGA ACCGACGGAG GCCACACAGT CAGTAACCGA GGACTTCCAA TGGAAGGTGT      360

CTTGGAAATA AGAGAGTTAA GATTTATACC AAGACTCCTA GAGAATTTTC GAAATGAATT      420

ATTCTACTTC GTCATGTTTC AATCTCGCTA CCGCCTGTAT CAGTAATTGG TGGCACAACC      480

CTGATGAGTT CCCGTACCAC CTTACATGTT GGCGATACTA CCTTAAGGAT ACAGAACCCT      540

ACTTGTACGA TAATGTAGAA CGTGACCACC TTCCCCATTG TTTTCGTGAC CTCTGTTGAA      600

ATTACCTCAA GGTTTATATC TAGTATGTGT TAGGAAACAA GCCTTTCTAG AGTAACTGAC      660

CTACGCCACC GATTCTAGGA GACAACCGAA GGTTCTAAAA GCAAAACTAA AACGGTTTCC      720

AATACGAAGT TTCATACATT TCCTTATATA GCTCCCTCGA CTCGGTTATA AACGTCAACC      780

TCTTATGACC CTGTGAACGT TAATGTTCCC GTCGTTAAAC CTAATGTTGG TTCTATCAGT      840

GTCCGTTTCT TAGTAGTTAA CCTAACTACC GCGCCCTGTT GAAAGTTGAC GTAAGCTAAA      900

ATGTTGTTTT CGTCAGGAAG TCCTTCGTCA GTTTCCTCTT AAGACCGCAA ACGCACTGAG      960

ATTCCCCTTC GGGGGTCCTC AAAATCCTAA CACCGGAAGT TCCCGACAGT GAAAATAACT     1020

ATTAGTGCTG TGACCTAGTT GAGTCCGCGT AACCGGAAAG GGAAGTGCAG TACAATACCT     1080

CCCGATACGT ATGTAAGAAT GTGTGGGTCC CTATGGTAGT CAAAAGAAAC TGGTAAAGAT     1140

GCTTACCCTA TTAAGGTACG TACTGGTTTA ACATTTCGAC TAACGATAAG CCTCCTTAGT     1200

TCCGTATGTG TCGGCAAGTA GATATTCTTA AGAACTCCGT GTCGGTTTGA ATATGCGACG     1260

TTGGTAACTA CTTTTCCAAT CGCACTTCTA ACCCCTGCCT AGTACCTCGG GACGACCCTT     1320

TCTCACCTGA GAGCGCTGGT CACCGGTAGC GATACGTCAG ACCGTCTTCA TTAGAATGTC     1380

GATAAGGCAA TGAATTATAT AATCATCTTT ATATATACAA AATTTGGGCT CGTGGATGAA     1440

GATTGTGATC TAGGCGGAGA TGTCCGAACC TACCTCACTA CTCAAAAAAA AAGGACAAGT     1500

AATCTGTAAC GTTGTACCCT ACATACAAAA CAATTATTTT CACAAGAACT AGTTACGTTA     1560

CATTATTCCC                                                           1570
```

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
GATAACATTA TGAAGGTGAT                                                  20
```

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GACGGCTGTG GGGTGGAGGA G                                                21
```

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CTTGTTATTT GAGTTACTCT C                                         21

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CATAAATTTG TGTCAAATTA TTAAAT                                    26

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

AGGGGTGAAT TGTATAATAT AAT                                       23

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GAAATATTTT TTTTGAAATG GAT                                       23

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

ATTATATTAT ACAATTCACC CCT                                       23

(2) INFORMATION FOR SEQ ID NO:27:

(i) SEQUENCE CHARACTERISTICS:
        (A) LENGTH: 21 base pairs
        (B) TYPE: nucleic acid -continued

```
        (C) STRANDEDNESS: single
        (D) TOPOLOGY: linear (ii) MOLECULE TYPE: cDNA (xi) SEQUENCE DESCRIPTION: SEQ ID NO:27:

CGCTTTCCCA CCAACGCTGA T                                             21
```